US008660651B2

(12) United States Patent
Castel et al.

(10) Patent No.: US 8,660,651 B2
(45) Date of Patent: Feb. 25, 2014

(54) ELECTRICAL STIMULATION METHOD FOR TREATMENT OF PERIPHERAL NEUROPATHY

(75) Inventors: J. Chris Castel, Reno, NV (US); Francis X. Palermo, Lafayette, CO (US)

(73) Assignee: Accelerated Care Plus Corp., Reno, NV (US)

( * ) Notice: Subject to any disclaimer, the term of this patent is extended or adjusted under 35 U.S.C. 154(b) by 804 days.

(21) Appl. No.: 12/164,875

(22) Filed: Jun. 30, 2008

(65) Prior Publication Data

US 2009/0326607 A1 Dec. 31, 2009

(51) Int. Cl.
*A61N 1/18* (2006.01)

(52) U.S. Cl.
USPC ............................................... 607/46; 607/48

(58) Field of Classification Search
USPC ...................................................... 607/46–48
See application file for complete search history.

(56) References Cited

U.S. PATENT DOCUMENTS

| | | | | |
|---|---|---|---|---|
| 5,556,422 | A * | 9/1996 | Powell et al. | 607/48 |
| 5,562,718 | A * | 10/1996 | Palermo | 607/46 |
| 5,713,923 | A * | 2/1998 | Ward et al. | 607/3 |
| 5,823,969 | A * | 10/1998 | Christy | 600/557 |
| 6,607,550 | B1 | 8/2003 | Bertwell | |
| 6,884,770 | B1 * | 4/2005 | Galdes et al. | 514/6.9 |
| 7,162,305 | B2 * | 1/2007 | Tong et al. | 607/48 |
| 2004/0158297 | A1 * | 8/2004 | Gonzalez | 607/45 |
| 2007/0156182 | A1 * | 7/2007 | Castel et al. | 607/2 |
| 2007/0259960 | A1 * | 11/2007 | Klaus et al. | 514/574 |

OTHER PUBLICATIONS

PCT/US09/44928 International Search Report and Written Opinion dated Jul. 1, 2009.
U.S. Appl. No. 61/073,653, filed Jun. 18, 2008, Castel et al.
Petterson et al., *The use of patterned neuromuscular stimulation to improve hand function following surgery for ulnar neuropathy*, J. Hand Surg. Aug;19(4) 430-433 (1994) [Abstract only].
Palermo, *Electrical Stimulation Strength Increase in Charcot-Marie-Tooth Diseases*, 77 Archives of Physical Medicine and Rehabilitation (1996).
Kumar, *Diabetic Peripheral Neuropathy: Amelioration of Pain with Transcutaneous Electrostimulation*, 20 Diabetes Care 1702 (1997) [Abstract only].
Julka et al., *Beneficial effects of electrical stimulation on neuropathic symptoms in diabetes patients*, J Foot Ankle Surg. May-Jun;37(3) 191-194 (1998) [Abstract only].
Alvaro et al., *Transcutaneous Electrostimulation: Emerging Treatment for Diabetic Neuropathic Pain*, 1 Diabetes Technology & Therapeutics 77 (1999) [Abstract only].

(Continued)

*Primary Examiner* — Rex R Holmes
(74) *Attorney, Agent, or Firm* — Stinson Leonard Street LLP

(57) ABSTRACT

An electrical stimulation method for the treatment of peripheral neuropathy is disclosed. In a preferred embodiment, the method utilizes an electrical stimulation device that includes a plurality of channels of electrodes each of which includes a first and second electrode positioned in electrical contact with tissue of a target region suffering from peripheral neuropathy. Agonist/antagonist muscles involved in abduction/adduction, flexion/extension, supination/pronation, protraction/retraction, and/or eversion/inversion in the peripheral body regions are stimulated with a patterned series of electrical pulses through channels of electrodes in accordance with a procedure for treating peripheral neuropathy. The patterned series of electrical pulses may comprise: a plurality of cycles of a biphasic sequential pulse train pattern; a plurality of cycles of a biphasic overlapping pulse train pattern; a plurality of cycles of a triphasic sequential pulse train pattern; and a plurality of cycles of a triphasic overlapping pulse train pattern.

26 Claims, 6 Drawing Sheets

10 12 14 16 22 24 28 30 18 20 Channel A Channel B 26 26a 26b 32 18a 18b 32a 32b 20a 20b

(56) References Cited

OTHER PUBLICATIONS

Somers et al., *Treatment of Neuropathic Pain in a Patient With Diabetic Neuropathy Using Transcutaneous Electrical Nerve Stimulation Applied to the Skin of the Lumbar Region*, Physical Therapy, 79(8) 767-775 (1999).

Hamza et al., *Percutaneous Electrical Nerve Stimulation: A Novel Analgesic Therapy for Diabetic Neuropathic Pain*, 23 Diabetes Care 365 (2000).

Inoue et al., *Long-lasting effect of transcutaneous electrical nerve stimulation on the thermal hyperalgesia in the rat model of peripheral neuropathy*, J Neurol Sci., Jul. 15; 211(1-2) 43-47 (2003) [Abstract only].

Oyibo et al., Electrical stimulation therapy through stocking electrodes for painful diabetic neuropathy: a double blind, controlled crossover study, Diabet. Med. Aug. 21(8) 940-944 (2004) [Abstract only].

Bosi et al., *Effectiveness of Frequency-modulated Electromagnetic Neural Stimulation in the Treatment of Painful Diabetic Neuropathy*, 48 Diabetologia 817 (2005) [Abstract only].

Reichstein et al., *Effective Treatment of Symptomatic Diabetic Polyneuropathy by High-frequency External Muscle Stimulation*, 48 Diabetologia 824 (2005).

* cited by examiner

ELECTRICAL STIMULATION METHOD FOR TREATMENT OF PERIPHERAL NEUROPATHY

CROSS-REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The present invention is generally directed to the treatment of peripheral neuropathy, and is more specifically directed to an electrical stimulation method for applying a patterned series of electrical pulses to a plurality of channels of electrodes in accordance with a procedure for treating peripheral neuropathy. The treatment results in improved sensation in a patient as demonstrated directly or indirectly by improved vibration perception, improved balance, increased muscle strength, increased muscle work output, and/or increased functional performance.

DESCRIPTION OF RELATED ART

Peripheral neuropathy is a general term referring to disorders of the peripheral nervous system. The peripheral nervous system is made up of the nerves that branch out of the spinal cord to all parts of the body. Impaired function and symptoms depend on the type of nerves (motor, sensory, or automatic) that are damaged. Sensory nerve fiber damage is more likely to generate various sensations, while motor nerve fiber damage is more apt to result in weakening and wasting of muscle tissue in the affected area. Thus, some people may experience temporary numbness, tingling, and pricking sensations, sensitivity to touch, or muscle weakness. Others may suffer more extreme symptoms, including burning pain (especially at night), muscle wasting, paralysis, or organ or gland dysfunction.

Peripheral neuropathy also can be classified by where it occurs in the body. Nerve damage that occurs in one area of the body is called mononeuropathy. When the damage is in many areas, the term is polyneuropathy. When the disorder occurs in the same place on both sides of the body, the condition is called symmetric neuropathy.

More than 100 types of peripheral neuropathy have been reported, each with its own characteristic pattern of development, symptoms, and prognosis. Peripheral neuropathy may be either inherited or acquired. Causes of peripheral neuropathy include, but are not limited to: nerve compression, entrapment or laceration (e.g., crutches, ulnar neuropathy, thoracic outlet syndrome, meralgia paresthetica, Morton's metatarsalgia); metabolic (diabetes mellitus, hypothyroidism) and autoimmune disorders (lupus, rheumatoid arthritis, Guillain-Barre Syndrome, Miller Fisher Syndrome); kidney disease, liver disease, toxin-induced (alcohol, tobacco, asbestos, arsenic, lead, mercury); malignant lymphoma; lung cancer; viral or bacterial infections (HIV, Lyme disease, leprosy, poliomyelitis); medication-induced (chemotherapy); trauma; repetition (carpal tunnel syndrome, cubital tunnel syndrome); and vitamin deficiency (especially vitamin B). Inherited causes include Charcot-Marie Tooth, Kennedy's disease (X-linked bilbospinal muscular atrophy), Van Allen's Syndrome (hereditary amyloid neuropathy), Refsum's disease, and Tangier disease.

Peripheral neuropathy has been conventionally treated with medication, injection therapy, physical therapy, surgery, and light. More recently, diabetic peripheral neuropathy has been treated by applying a surface electrical stimulation at a specified frequency to the muscles and nerves. See, e.g., Emanuele Bosi et al., *Effectiveness of Frequency-modulated Electromagnetic Neural Stimulation in the Treatment of Painful Diabetic Neuropathy,* 48 Diabetologia 817 (2005); L. Reichstein et al., *Effective Treatment of Symptomatic Diabetic Polyneuropathy by High-frequency External Muscle Stimulation,* 48 Diabetologia 824 (2005); M. A. Hamza et al., *Percutaneous Electrical Nerve Stimulation: A Novel Analgesic Therapy for Diabetic Neuropathic Pain,* 23 Diabetes Care 365 (2000) (percutaneous electrical nerve stimulation using an alternating frequency of 15 and 30 Hz); Michael Alvaro et al., *Transcutaneous Electrostimulation: Emerging Treatment for Diabetic Neuropathic Pain,* 1 Diabetes Technology & Therapeutics 77 (1999); and Dinesh Kumar & H. J. Marshall, *Diabetic Peripheral Neuropathy: Amelioration of Pain with Transcutaneous Electrostimulation,* 20 Diabetes Care 1702 (1997) (H-wave machine: pulse width 4 milliseconds, frequency greater than 2 Hz). This prior use of electrical stimulation has involved the use of relatively wide pulse widths having a constant frequency.

Additionally, peripheral neuropathy has been treated by applying surface electrical stimulation in functional pulse train patterns. See Francis X. Palermo, *Electrical Stimulation Strength Increase in Charcot-Marie-Tooth Disease,* 77 Archives of Physical Medicine and Rehabilitation (1996). The functional pulse train patterns often simulate walking or cycling patterns and are generally used for major muscle groups suffering from less advanced stages of peripheral neuropathy.

The present invention is directed to the treatment of peripheral neuropathy with the application of electrical pulses in a specific pulse train pattern to nerves and muscles. In particular, the present invention uses a biphasic or triphasic pulse train pattern. In an exemplary embodiment, the pulse width is about 30 to 100 microseconds the frequency of a phase is about 30 to 100 Hz, and the pulse train duration is about 100 to 200 microseconds.

BRIEF SUMMARY OF THE INVENTION

The present invention is directed to an electrical stimulation method for the treatment of peripheral neuropathy. In general, the electrical stimulation method utilizes an electronic control unit connected to two or more channels of electrodes, such as transcutaneous or percutaneous electrodes. Each channel comprises two electrodes (i.e., a relative positive electrode and a relative negative electrode), wherein one electrode is positioned in electrical contact with a first tissue of a target region of a patient and the other electrode is positioned in electrical contact with a second tissue of a target region of a patient. The electrical control unit applies a series of electrical pulses to a patient through the two or more channels of electrodes in accordance with a procedure for treating peripheral neuropathy.

In one aspect, the electrical stimulation method stimulates the sensory and motor nerves of the patient's musculature, such as the muscles of the lower extremities or upper extremities. Often, the electrodes are positioned bilaterally or in electrical contact with tissue of agonist/antagonist muscle pairs in the arm, forearm, wrist, hand, thigh, lower leg, ankle, or foot of the patient. Examples of agonist/antagonist muscle pairs include abductors/adductors, flexors/extensors, supinators/pronators, protractors/retractors, and vectors/inverters. For example, both the flexor carpi radialis and flexor carpi ulnaris are flexors of the wrist. The extensor carpi radialis longus, in conjunction with extensor carpi radialis brevis, is an extensor of the wrist.

In a first embodiment, the electrical stimulation method can be used to stimulate the muscles associated with toe extension/flexion and ankle dorsiflexion/plantar flexion. For example, the electrodes are positioned in electrical contact with tissue to stimulate a motor point of a patient's extensor digitorum brevis, tibialis anterior, extensor digitorum longus, extensor hallucis longus, posterior tibialis, flexor hallucis, and/or intrinsic foot muscles including abductor hallucis muscle.

In a second embodiment, the electrical stimulation method can be used to stimulate the muscles associated with ankle dorsiflexion and plantar flexion and ankle inversion/eversion. For example, the electrodes are positioned in electrical contact with tissue to stimulate a motor point of a patient's tibialis anterior, triceps surae including gastrocnemius and soleus muscles, and/or anterior and lateral muscles of the leg, including the peroneus muscle.

In a third embodiment, the electrical stimulation method can be used to stimulate the muscles associated with wrist extension/flexion, wrist pronation/supination, and finger extension/flexion. For example, the electrodes are positioned in electrical contact with tissue to stimulate a motor point of a patient's flexor digitorum superficialis, flexor carpi radialis, flexor carpi ulnaris, extensor digitorum, pollicis, extensor digiti minimi, extensor carpi ulnaris, extensor carpi radialis longus, and/or carpi radialis brevis muscles.

In a fourth embodiment, the electrical stimulation method can be used to stimulate the muscles associated with elbow flexion/extension. For example, the electrodes are positioned in electrical contact with tissue to stimulate a motor point of a patient's biceps brachii and triceps brachii muscles.

In a fifth embodiment, the electrical stimulation method can be used to stimulate the muscles associated with movement of the upper extremities. For example, the electrodes are positioned in electrical contact with tissue to stimulate a motor point of a patient's biceps brachii muscles, triceps brachii muscles, intrinsic hand muscles, and/or extensor muscles of the forearm.

In a sixth embodiment, the electrical stimulation method can be used to stimulate the muscles associated with ankle dorsiflexion and plantar flexion and ankle inversion/eversion. For example, the electrodes are positioned in electrical contact with tissue to stimulate a motor point of a patient's tibialis anterior, peroneus, triceps surae, and/or lumbricales muscles.

In a seventh embodiment, the electrical stimulation method can be used to stimulate the muscles associated with movement of the lower extremities. For example, the electrodes are positioned in electrical contact with tissue to stimulate a motor point of a patient's tibialis anterior, quadriceps, triceps surae, and/or hamstring muscles.

In an eighth embodiment, the electrical stimulation method can be used to stimulate the muscles associated with knee flexion/extension. For example, the electrodes are positioned in electrical contact with tissue to stimulate a motor point of a patient's rectus femoris, vastus lateralis, vastus medialis, biceps femoris, semimembranosus, and/or semitendinosus muscles.

The series of electrical pulses applied to the one or more channels of electrodes may comprise a variety of different types of biphasic or triphasic pulse train patterns. For example, a plurality of cycles of a biphasic sequential or overlapping pulse train pattern may be used, in which a first phase of electrical pulses is applied to a first channel of electrodes, and a second phase of electrical pulses is applied to a second channel of electrodes. Using the biphasic sequential pulse train pattern, the second phase of electrical pulses commences after termination of the first phase of electrical pulses such that there is a time delay there between. Using the biphasic overlapping pulse train pattern, the second phase of electrical pulses commences before termination of the first phase of electrical pulses such that there is an overlap there between.

In another example, a plurality of cycles of a triphasic sequential or overlapping pulse train pattern may be used, in which a first phase of electrical pulses is applied to a first channel of electrodes, a second phase of electrical pulses is applied to a second channel of electrodes, and a third phase of electrical pulses is applied to the first channel of electrodes. Using the triphasic sequential pulse train pattern, the second phase of electrical pulses commences after termination of the first phase of electrical pulses such that there is a time delay there between, and, similarly, the third phase of electrical pulses commences after termination of the second phase of electrical pulses such that there is a time delay there between. Using the triphasic overlapping pulse train pattern, the second phase of electrical pulses commences before termination of the first phase of electrical pulses such that there is an overlap there between, and, similarly, the third phase of electrical pulses commences before termination of the second phase of electrical pulses such that there is an overlap there between.

In one aspect of the present invention, treatment of peripheral neuropathy in a patient is demonstrated by increased sensation, which can be shown directly using sensation threshold tests. One test for a patient's sensation threshold is the Semmes Weinstein monofilament test. In general, the monofilaments generate a reproducible buckling stress and are identified by manufacturer-assigned numbers, for example, those ranging from 1.65 to 6.65. The higher the number of the monofilament, the stiffer and more difficult it is to bend, according to the formula: nominal value=log10 [force (in milligrams)×10]. Three monofilaments commonly used to screen patients at risk for peripheral neuropathy are the 4.32 (2 g), the 5.07 (10 g), and the 6.10. Other monofilaments commonly used include the 3.22, 3.84, 4.08, 4.17, 4.31, 4.56, 4.74, 4.93, 5.07, 5.18, 5.46, 5.88, 6.10, and 6.45. The monofilaments can be used to measure a patient's ability to sense a point of stress. In a preferred aspect, a Semmes Weinstein monofilament test is conducted on the sole of the foot, particularly on areas of the sole innervated by the lateral plantar nerve and the medial plantar nerve. The filament is applied until it begins to bend and is held in place for about 1.5 seconds. The lower the number of the monofilament that elicits a sensory response, the more sensation the patient is capable of perceiving at that point.

In another aspect of the present invention, treatment of peripheral neuropathy in a patient is demonstrated by improved sensation, which is indirectly shown by improved vibration perception. One test for quantifying a patient's vibration perception threshold can be performed during a clinical examination with a tuning fork (e.g., 128 Hz) placed over a target region, e.g., a toe, finger pad, joint of the foot, ankle, tibia, finger, or wrist. Patients indicate to the examiner when they feel the vibration or when it diminishes and disappears. The length of time a patient can perceive the vibration after the tuning fork is forcefully struck can be measured in seconds. Another commonly used device for quantifying vibration perception is known as a biothesiometer. A biothesiometer assesses the function of large axons (fibers) of a peripheral nerve carrying the sensations of position and vibration. A biothesiometer has a stimulator that delivers vibrations of various amplitudes through one or more probes or filaments applied to the skin over a finger pad or an extremity joint with a constant frequency of vibration (e.g., 100 Hz). As the amplitude of vibration is gradually increased, patients indicate to the examiner the point at which they have vibration sensation. Conversely, as the amplitude of vibration is gradually decreased, patients report when vibration is no longer discernable. The threshold of vibration sensation may be measured in volts or in the amplitude of vibration which is proportional to the square of the applied voltage.

In another aspect of the present invention, treatment of peripheral neuropathy in a patient is demonstrated by improved sensation, which is indirectly shown by improved balance. Impaired balance is a symptom of the disease because as a patient loses sensation in a body region, the patient's ability to balance decreases. One way to measure balance is to use Visual Analogue Scales ("VAS"). VAS are generally horizontal lines, for example, 100 mm in length, anchored at each end by word descriptors such as "No difficulty balancing" and "Very difficult to balance." Patients mark on the line the point that they feel represents their perception of their current state. The VAS score is determined by measuring in millimeters from the left hand end of the line to the point that the patient marks. Use of VAS is particularly valuable when looking at change within individuals.

Another way to measure balance is to use the Berg Balance Test ("BBT"). The BBT requires a patient to perform 14 different actions including: transitioning from sitting to standing, standing unsupported, sitting unsupported with feet on the floor, transitioning from standing to sitting, transferring from a chair with arm rests to a chair with no arm rests, standing unsupported with eyes closed, standing unsupported with feet together, reaching forward with outstretched arm, picking up an object from the floor, turning to look behind over left and right shoulders, turning 360 degrees, counting the number of times a step stool is touched with each foot alternatively, standing unsupported with one foot directly in front of the other, and standing on one leg unsupported. For each action, the patient is rated on a scale of zero to four (zero indicates a lack of balance and four indicates sufficient balance).

A third way to measure balance is to use the unipedal stance test. The unipedal stance test quantifies a patient's static balance ability by measuring the length of time a patient can stand on one foot, unassisted, first with the patient's eyes open, and then with the patient's eyes closed. Time commences when the patient raises one foot off the floor and time ends when the patient uses the arms or the raised foot, moves the weight-bearing foot, a maximum of 45 seconds elapses, or when the patient opens the patient's eyes in the closed eyes portion of the test. Longer unipedal stance times indicate better balance.

A fourth way to measure balance is the functional reach test. The functional reach test measures the difference, in inches, between an arm's length measurement and a maximal forward reach measurement. A yardstick is placed at humeral head height, perpendicular to the patient's body when viewed from the side. The arm's length measurement is taken on the yardstick when the patient's shoulder is approximately at 90 degrees flexion (arm is parallel to the yardstick) with no scapular protraction. The maximal forward reach measurement is taken on the yardstick when the patient reaches forward as far as the patient can without touching the yardstick or taking a step forward. A functional reach test measurement of one to six inches generally indicates a lack of balance (high risk for falling), a measurement of six to ten inches indicates some lack of balance (moderate risk of falling), and a measurement of greater than ten inches indicates sufficient balance (low risk of falling).

In another aspect of the present invention, treatment of peripheral neuropathy in a patient is demonstrated by improved sensation, which is indirectly shown by increased strength. Decreased strength is a symptom of peripheral neuropathy because as a patient loses sensation in part of the body, the muscle groups that control movement of that part of the body decrease in strength through non-use. The strength of the muscle groups controlling a joint in the body is measured by the torque, or rotational force the joint is capable of exerting. The U.S. customary unit for torque is pounds feet (ft-lbs). Torque can be measured manually by recording the speed a patient can lift a specific amount of weight over a given rotational distance or automatically using isokinetic dynamometers such as the LIDO Active system, commercially available from Loredan Biomedical, Inc., 3650 Industrial Blvd., Sacramento, Calif. 95691, or the Biodex system, commercially available from Biodex Medical Systems, Inc., 20 Ramsay Road, Shirley, N.Y. 11967-4704.

In another aspect of the present invention, treatment of peripheral neuropathy in a patient is demonstrated by improved sensation, which is indirectly shown by increased work output. Decreased work output is a symptom of peripheral neuropathy because as a patient loses sensation in part of the body, the work output of the muscle groups that control the movement of that part of the body decreases through non-use. Muscle work output is measured by the endurance the muscle exhibits. Endurance can be measured by the length of time a patient can perform movement of a fixed amount under a load.

In another aspect of the present invention, treatment of peripheral neuropathy in a patient is demonstrated by improved sensation, which is indirectly shown by improved functional performance, such as with activities of daily living. Impaired functional performance is a symptom of peripheral neuropathy because as a patient loses sensation in a region of the body, the patient's ability to perform specific functions that require use and coordination of that part of the body is impaired. One type of functional performance test is having a patient sit in a chair, stand up, walk a specific course, return to the chair, and sit back down in the chair.

The peripheral neuropathy treatment methods of the present invention are well-adapted to be used with other conventional therapies for peripheral neuropathy treatment, including, but not limited to: corticosteroids; IV immunoglobulins; plasma exchange or plasmapheresis; immunosuppressive agents; surgery; mechanical aids; avoiding toxins including alcohol; aldose reductase inhibitors; fish oil; gamma-linolenic acid; gangliosides; lipoic acid; myoinositol; nerve growth factor; protein kinase C inhibitors; pyridoxine; ruboxistaurin mesylate; thiamine; vitamin B12; pain relievers including codeine; anti-seizure medications including gabapentin, topiramate, pregabalin, carbamazepine, and phenytoin; topical anesthetics such as lidocaine; tricyclic antidepressant medications such as amitriptyline and nortriptyline; selective serotonin and norepinephrine reuptake inhibitors such as duloxetine; and mexiletine. The agents may also include, for example, dopamine uptake inhibitors, monoamine oxidase inhibitors, norepinephrine uptake inhibitors, dopamine agonists, acetocholinesterase inhibitors, catechol O-methyltransferase inhibitors, anticholinergic agents, antioxidants, as well as synaptic and axonal enhancing medications.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

The present invention will be described in greater detail in the following detailed description of the invention with reference to the accompanying drawings that form a part hereof, in which.

DETAILED DESCRIPTION OF PREFERRED EMBODIMENT

Figure 1:
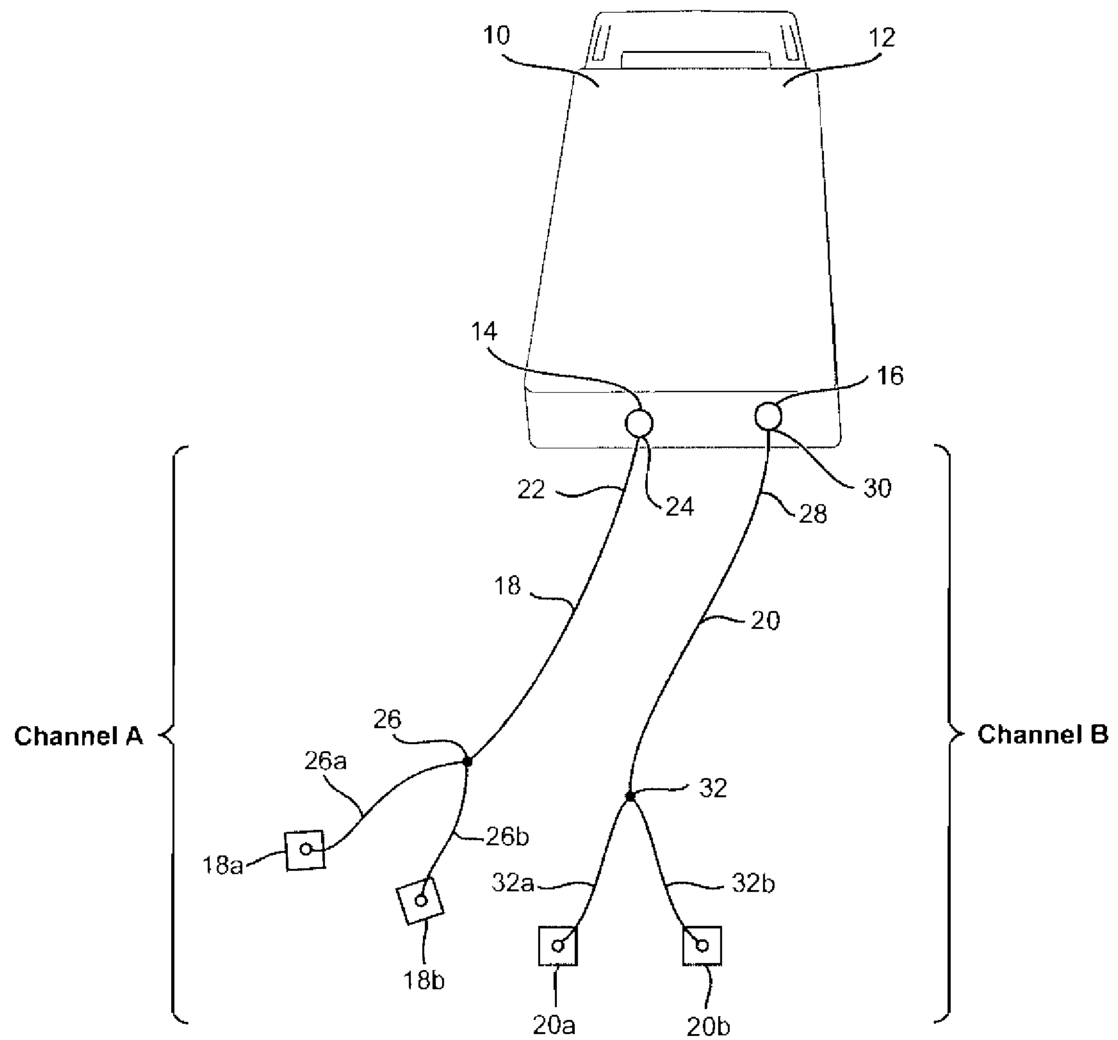
FIG. 1 is a block diagram of an electrical stimulation device that may be used in accordance with the method of the present invention.

The present invention is directed to an electrical stimulation method for the treatment of peripheral neuropathy.

As used herein, the term "administration" refers to a method of giving an agent to a patient, where the method is, e.g., topical, oral, intravenous, transdermal, intraperitoneal, or intramuscular. The preferred method of administration can vary depending on various factors, e.g., the components of the pharmaceutical composition.

As used herein, "concurrent administration," "co-administration," or "co-treatment" includes administration of the agents or application of the electrical stimulation treatment method together, or before or after each other. The therapeutic agents co-administered with the electrical stimulation treatment methods may be administered by the same or different routes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "therapeutically effective amount" as used herein, means that amount of an active agent which, alone or in combination with other drugs, provides a therapeutic benefit in the prevention, treatment, or management of peripheral neuropathy. Different therapeutically effective amounts may be readily determined by those of ordinary skill in the art.

As used herein, the term "electrical stimulation" refers to the passing of various types of current to a patient through transcutaneous or percutaneous electrodes, and includes muscle activation by stimulation of the nerves innervating the sensory (cutaneous and position sensors) and muscle fibers associated with central pattern generator inputs or inhibitory mechanism and stimulation of motor efferent fibers which activate the muscles.

Examples of the types of electrical stimulation that may be used include, but are not limited to: Patterned Electrical Neuromuscular Stimulation (PENS); Transcutaneous Electrical Nerve Stimulation (TENS); Neuromuscular Electrical Stimulation (NMES); Interferential Current (IFC); Percutaneous Electrical Muscle Stimulation (PEMS); Percutaneous Nerve Stimulation (PENS); and pulsed magnetic field neuromuscular depolarization systems, which each may use alternating or modulated alternating current waveforms, asymmetrical or symmetrical biphasic pulsed current waveforms and monophasic pulsed current waveforms. Of course, one skilled in the art will appreciate that other types of electrical stimulation may also be used in accordance with the present invention.

As used herein, the term "motor point" refers to an area of tissue that can be electrically stimulated by lower levels of electricity compared to surrounding areas. The motor point overlies the innervated zone of a muscle where the motor nerve endings are concentrated or where the nerve trunk enters the muscle. The motor point is often used as a placement site for surface electrodes used to stimulate the muscle.

As used herein, the term "tissue" refers to an aggregation of morphologically similar cells and associated intercellular matter acting together to perform one or more specific functions in the body, including epithelial, connective, muscle, and neural tissue.

As used herein, the term "treatment" refers to the treatment of peripheral neuropathy, in a patient, such as a mammal (particularly a human), which includes preventing, ameliorating, suppressing, or alleviating one or more of the symptoms of peripheral neuropathy such as impaired sensation demonstrated directly or indirectly by impaired vibration sensation, impaired balance, decreased muscle strength, decreased muscle work output, and impaired functional performance. In a preferred aspect, the treatment of the present invention results in the reactivation of the nerve. The term reactivation means the ability of the nerve to depolarize and conduct signals.

As used herein, the term "agonist muscle" broadly refers to a muscle that is resisted or counteracted by another muscle, the "antagonist muscle." Examples of agonist/antagonist muscle pairs include abductors/adductors, flexors/extensors, supinators/pronators, protractors/retractors, and evertors/inverters.

As used herein, the term "abductors" refers to muscles that generally cause movement away from the body centerline while "adductors" are muscles that generally cause movement toward the body centerline.

As used herein, the term "flexors" refers to muscles that generally reduce the angle of a joint, while "extensors" refers to muscles that increase the angle of the joint. For example, both the flexor carpi radialis and flexor carpi ulnaris are flexors of the wrist. The extensor carpi radialis longus, in conjunction with extensor carpi radialis brevis, is an extensor of the wrist.

As used herein, the term "pronator" refers to a muscle that causes the twisting movement of the wrist that turns the palm from facing front to facing back. The opposing movement, which turns the palm from facing back to facing front, is directed by a "supinator."

As used herein, the term "protractor" is a muscle that moves a part of the body anterior in the horizontal plane while a "retractor" muscle is involved in the reverse movement.

As used herein, the term "evertor" refers to a muscle involved in the twisting motion of the foot that turns the sole outward while the opposite movement of turning the sole inward is performed by an "inverter" muscle.

Referring to FIG. 1, an exemplary embodiment of an electrical stimulation device that may be used in accordance with the method of the present invention is designated generally as reference numeral 10. Electrical stimulation device 10 generally comprises an electronic control unit 12 with a plurality of output connectors 14, 16, which are connected to a plurality of output cables 18, 20 and associated electrode pairs 18*a*, 18*b*, and 20*a*, 20*b*, respectively. Although two output connectors 14, 16 are shown in FIG. 1, it should be understood that electronic control unit 12 may include any number of output connectors (such as two, four, six, or eight output connectors) in accordance with the present invention.

Output cables 18, 20 each comprise any suitable type of insulated conductive cable, such as a coaxial cable. In the illustrated embodiment, output cable 18 includes a back section 22 with a connector 24 (such as a male jack) that attaches to output connector 14, and a front section 26 that splits into a first split end 26*a* and a second split end 26*b*. Similarly, output cable 20 includes a back section 28 with a connector 30 (such as a male jack) that attaches to output connector 16, and a front section 32 that splits into a first split end 32*a* and a second split end 32*b*. Of course, it should be understood that each of the output cables 18, 20 could alternatively be manufactured out of two separate leads (instead of having a front section with split ends). In addition, output cables 18, 20 could be connected directly to electronic control unit 12 without the use of connectors.

As can be seen in FIG. 1, electrodes 18*a*, 18*b* are attached to split ends 26*a*, 26*b* of output cable 18, respectively. Similarly, electrodes 20*a*, 20*b* are attached to split ends 32*a*, 32*b* of output cable 20, respectively. As such, output cable 18 and electrodes 18*a*, 18*b* together form a first output channel (referred to hereinafter as "channel A"), and output cable 20 and electrodes 20*a*, 20*b* together form a second output channel (referred to hereinafter as "channel B"). Although two channels are shown in FIG. 1, it should be understood that any number of channels (e.g., four, six, or eight channels) may be used in accordance with the present invention (provided, of course, that the number of channels corresponds to the number of output connectors of electronic control unit 12).

In the illustrated example, electrodes 18*a* and 20*a* each comprise a relative positive electrode, and electrodes 18*b* and 20*b* each comprise a relative negative electrode. As will be described in greater detail herein below, each of the electrical pulses applied to electrodes 18*a*, 18*b* and electrodes 20*a*, 20*b* may comprise, for example, a monophasic waveform (which has absolute polarity), a biphasic asymmetric waveform (which has relative polarity), or a biphasic symmetric waveform (which has no polarity). Thus, as used herein, the term "positive electrode" refers to a relative positive electrode and the term "negative electrode" refers to a relative negative electrode (regardless of whether the electrical pulse comprises a monophasic waveform, an asymmetric biphasic waveform, or a symmetric biphasic waveform which behaves like the relative positive or relative negative electrode during each phase of the waveform).

Electrodes 18*a*, 18*b* and 20*a*, 20*b* are each adapted to be positioned in electrical conduct with tissue of selected regions of a patient, as will be described in greater detail herein below with reference to FIG. 3A-3H. In the illustrated embodiment, each of electrodes 18*a*, 18*b* and 20*a*, 20*b* comprises a transcutaneous electrode having a surface electrode pad that may be placed on the skin of a patient. As is known in the art, each of electrodes 18*a*, 18*b*, and 20*a*, 20*b* may be formed of metal or some other physiologically acceptable conductive material and may take on a variety of different sizes and shapes. Of course, one or more of electrodes 18*a*, 18*b* and 20*a*, 20*b* may alternatively comprise a percutaneous electrode, such as a needle electrode, or any other type of suitable electrode in accordance with the present invention.

Electronic control unit 12 also includes internal circuitry (not shown) for selectively generating a series of electrical pulses in accordance with a procedure for treating peripheral neuropathy. The series of electrical pulses generated by the circuitry are provided at output connectors 14, 16 and, as such, may be applied to a patient through channel A and/or channel B. The series of electrical pulses may comprise a variety of different types of pulse train patterns, such as: a plurality of cycles of a biphasic sequential pulse train pattern; a plurality of cycles of a biphasic overlapping pulse train pattern; a plurality of cycles of a triphasic sequential pulse train pattern; or a plurality of cycles of a triphasic overlapping pulse train pattern. Each of these pulse train patterns will be described in detail herein below with reference to FIGS. 2A-2D. One skilled in the art will understand that a variety of different circuit configurations may be used to generate the various pulse train patterns, such as the circuitry described in Palermo, U.S. Pat. No. 5,562,718, which is incorporated herein by reference.

A variety of different electrical stimulation devices may be used and/or adapted for use in accordance with the present invention. For example, one may incorporate the protocols disclosed herein into the Omnistim® FX$^2$ patterned electrical neuromuscular stimulator or the Omnistim® FX$^2$ Pro patterned electrical neuromuscular stimulator, both of which are commercially available from Accelerated Care Plus, 4850 Joule Street, Suite A-1, Reno, Nev. 89502. Of course, other types of electrical stimulation devices could also be used, which are generally available in the industry.

Referring now to FIGS. 2A-2D, examples of the various types of pulse train patterns that may be used in accordance with the present invention will now be described herein below. Each of the pulse train patterns is comprised of a series of individual electrical pulses arranged into a particular pattern. Each of the electrical pulses may comprise either a monophasic or biphasic waveform, which may be, for example, asymmetric, symmetric, square, sinusoidal, and the like. Preferably each of the electrical pulses comprises a biphasic asymmetric square wave having a pulse duration that ranges between 30 microseconds and 100 microseconds during the positive phase and a current amplitude that typically ranges between 25 milliamps and 140 milliamps.

It has been found that electrical pulses having a short pulse duration and high current amplitude selectively trigger p-type calcium channels (preferably having a pulse duration of 30 microseconds to 100 microseconds and a current amplitude of 25 milliamps to 140 milliamps). Activation of p-type calcium channels allows calcium to flow into the neuron's cytosol and triggers the release of neurotransmitters. This repeated p-type calcium channel activation increases the neurotransmitter pool at the neuromuscular junction, which facilitates enhanced muscle recruitment. Twitch contractions may increase in intensity during the treatment even though the stimulation output is not increased as observed empirically. The additional calcium in the neuron's cytosol lasts for several hours post-treatment, which facilitates voluntary movement. This electrical stimulation results in both short and long-term NGF potentiation.

Biphasic Sequential Pulse Train Pattern

Figure 2A:
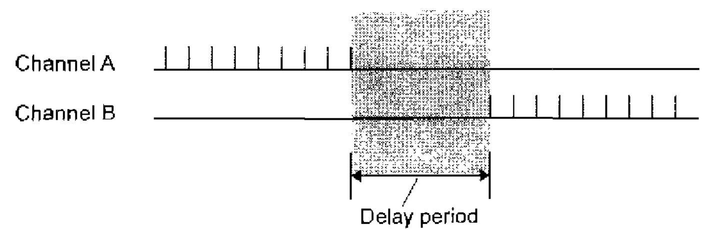
FIG. 2A is a timing diagram of a biphasic sequential pulse train pattern that may be applied to the output channels of the electrical stimulation device of FIG. 1.

Referring to FIG. 2A, electrical stimulation device 10 may be used to apply a plurality of cycles of a biphasic sequential pulse train pattern to a patient. In a typical biphasic sequential pulse train pattern, a first phase of electrical pulses is applied to channel A and a second phase of electrical pulses is applied to channel B with a delay period there between.

In the illustrated example, the first phase of electrical pulses is applied to channel A for approximately 60 milliseconds to 120 milliseconds (and most preferably about 100 milliseconds). At the conclusion of the first phase of electrical pulses, there is a delay period of approximately 0 milliseconds to 100 milliseconds (and most preferably about 80 milliseconds) before the second phase of electrical pulses is applied to channel B. Then, the second phase of electrical pulses is applied to channel B for approximately 60 milliseconds to 120 milliseconds (and most preferably about 100 milliseconds). The frequency of the individual electrical pulses in each phase is approximately 30 Hz to 100 Hz (and most preferably about 50 Hz).

The biphasic sequential pulse train pattern described above may be repeated approximately every 0.33 seconds (3 Hz) to 3 seconds (0.33 Hz). Preferably, the pulse train pattern is applied to the patient for a total treatment time of approximately 10 minutes to 60 minutes (and most preferably about 20 minutes to 30 minutes), as desired for a particular treatment.

Biphasic Overlapping Pulse Train Pattern

Figure 2B:
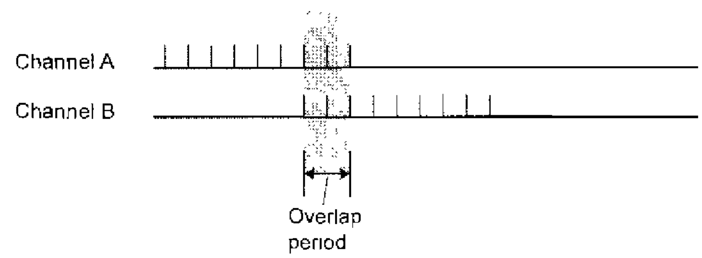
FIG. 2B is a timing diagram of a biphasic overlapping pulse train pattern that may be applied to the output channels of the electrical stimulation device of FIG. 1.

Referring to FIG. 2B, electrical stimulation device 10 may also be used to apply a plurality of cycles of a biphasic overlapping pulse train pattern to a patient. In a typical biphasic overlapping pulse train pattern, a first phase of electrical pulses is applied to channel A and a second phase of electrical pulses is applied to channel B with an overlap there between.

In the illustrated example, the first phase of electrical pulses is applied to channel A for approximately 60 milliseconds to 120 milliseconds (and most preferably about 100 milliseconds). When the first phase of electrical pulses has reached a time period of between 40 milliseconds and 100 milliseconds (and most preferably about 80 milliseconds), the second phase of electrical pulses is applied to channel B for approximately 60 milliseconds to 120 milliseconds (and most preferably about 100 milliseconds). Thus, there is an overlap of approximately 20 milliseconds to 80 milliseconds (and most preferably about 20 milliseconds) during which both channel A and channel B are providing electrical stimulation to the patient. The frequency of the individual electrical pulses in each phase is approximately 30 Hz to 100 Hz (and most preferably about 50 Hz).

The biphasic overlapping pulse train pattern described above may be repeated approximately every 0.33 seconds (3 Hz) to 3 seconds (0.33 Hz). Preferably, the pulse train pattern is applied to the patient for a total treatment time of approximately 10 minutes to 60 minutes (and most preferably about 20 minutes to 30 minutes), as desired for a particular treatment.

Triphasic Sequential Pulse Train Pattern

Figure 2C:
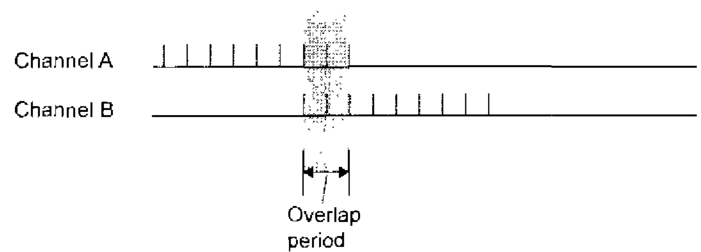
FIG. 2C is a timing diagram of a triphasic sequential pulse train pattern that may be applied to the output channels of the electrical stimulation device of FIG. 1.

Referring to FIG. 2C, electrical stimulation device 10 may also be used to apply a plurality of cycles of a triphasic sequential pulse train pattern to a patient. In a typical triphasic sequential pulse train pattern, a first phase of electrical pulses is applied to channel A, a second phase of electrical pulses is applied to channel B, and a third phase of electrical pulses is applied to channel A, wherein there is a delay period between the first and second phases of electrical pulses and another delay period between the second and third phases of electrical pulses.

In the illustrated example, the first phase of electrical pulses is applied to channel A for approximately 60 milliseconds to 120 milliseconds (and most preferably about 100 milliseconds). At the conclusion of the first phase of electrical pulses, there is a delay period of approximately 0 milliseconds to 100 milliseconds (and most preferably about 80 milliseconds) before the second phase of electrical pulses is applied to channel B. Then, the second phase of electrical pulses is applied to channel B for approximately 60 milliseconds to 120 milliseconds (and most preferably about 100 milliseconds). At the conclusion of the second phase of electrical pulses, there is a delay period of approximately 0 milliseconds to 100 milliseconds (and most preferably about 80 milliseconds) before the third phase of electrical pulses is applied to channel A. Then, the third phase of electrical pulses is applied to channel A for approximately 36 milliseconds to 72 milliseconds (and most preferably about 60 milliseconds). The frequency of the individual electrical pulses in each phase is approximately 30 Hz to 100 Hz (and most preferably about 50 Hz).

The triphasic sequential pulse train pattern described above may be repeated approximately every 0.33 seconds (3 Hz) to 3 seconds (0.33 Hz). Preferably, the pulse train pattern is applied to the patient for a total treatment time of approximately 10 minutes to 60 minutes (and most preferably about 20 minutes to 30 minutes), as desired for a particular treatment.

Triphasic Overlapping Pulse Train Pattern

Figure 2D:
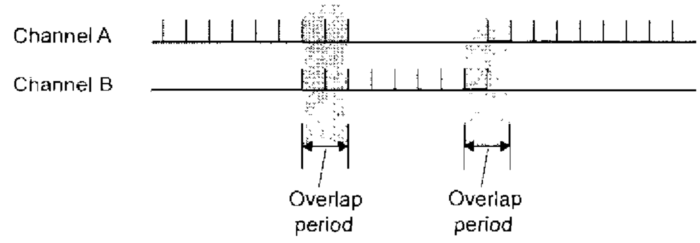
FIG. 2D is a timing diagram of a triphasic overlapping pulse train pattern that may be applied to the output channels of the electrical stimulation device of FIG. 1.

Referring to FIG. 2D, electrical stimulation device 10 may also be used to apply a plurality of cycles of a triphasic overlapping pulse train pattern to a patient. In a typical triphasic overlapping pulse train pattern, a first phase of electrical pulses is applied to channel A, a second phase of electrical pulses is applied to channel B, and a third phase of electrical pulses is applied to channel A, wherein there is an overlap period between the first and second phases of electrical pulses and another overlap period between the second and third phases of electrical pulses.

In the illustrated example, the first phase of electrical pulses is applied to channel A for approximately 60 milliseconds to 120 milliseconds (and most preferably about 100 milliseconds). When the first phase of electrical pulses has reached a time period of between 40 milliseconds and 100 milliseconds (and most preferably about 80 milliseconds), the second phase of electrical pulses is applied to channel B for approximately 60 milliseconds to 120 milliseconds (and most preferably about 100 milliseconds). Thus, there is an overlap period of approximately 20 milliseconds to 80 milliseconds (and most preferably about 20 milliseconds) during which both channel A and channel B are providing electrical stimulation to the patient. When the second phase of electrical pulses has reached a time period of between 40 milliseconds and 100 milliseconds (and most preferably about 80 milliseconds), the third phase of electrical pulses is applied to channel A for approximately 36 milliseconds to 72 milliseconds (and most preferably about 60 milliseconds) (i.e., the third phase of electrical pulses has a shorter time duration than that of the first phase of electrical pulses). Thus, there is an overlap of approximately 20 milliseconds to 72 milliseconds (and most preferably about 20 milliseconds) during which both channel B and channel A are providing electrical stimulation to the patient. The frequency of the individual electrical pulses in each phase is approximately 30 Hz to 100 Hz (and most preferably about 50 Hz).

The triphasic overlapping pulse train pattern described above may be repeated approximately every 0.33 seconds (3 Hz) to 3.0 seconds (0.33 Hz). Preferably, the pulse train pattern is applied to the patient for a total treatment time of approximately 10 minutes to 60 minutes (and most preferably about 20 minutes to 30 minutes), as desired for a particular treatment.

Referring now to FIGS. 3A-3H, electrodes 18*a*, 18*b*, and 20*a*, 20*b* are each adapted to be positioned in electrical contact with tissue of selected regions of a patient. The selected regions are preferably those that will assist in programming the central pattern generators associated with the muscles of the lower and upper extremities, such as those involved in toe extension/flexion, ankle dorsiflexion and plantar flexion, ankle eversion/inversion, wrist flexion/extension, finger flexion/extension, elbow flexion/extension, and knee extension/flexion. In the present invention, the muscle contractions produced by the pulse train patterns provide afferent inputs or efferent stimulation that assist in retraining the central nervous system and spinal motor loops to promote normal muscle function. In particular, it has been found that biphasic and triphasic pulse train pattern stimulation may assist in retraining the central pattern generators during the early stages of treatment of advanced stages of peripheral neuropathy. Additionally, biphasic and triphasic pulse train pattern stimulation may assist in retraining central pattern generators when functional pulse train patterns cannot be created either because of the difficulty in assessing the muscle groups involved or the research is too time consuming and costly.

The peripheral neuropathy treatment methods of the present invention are well-adapted to be used with other conventional therapies for peripheral neuropathy treatment, including but not limited to: corticosteroids; IV immunoglobulins; plasma exchange or plasmapheresis; immunosuppressive agents; surgery; mechanical aids; avoiding toxins including alcohol; aldose reductase inhibitors; fish oil; gamma-linolenic acid; gangliosides; lipoic acid; myoinositol; nerve growth factor; protein kinase C inhibitors; pyridoxine; ruboxistaurin mesylate; thiamine; vitamin B12; pain relievers including codeine; anti-seizure medications including gabapentin, topiramate, pregabalin, carbamazepine, and phenytoin; topical anesthetics such as lidocaine; tricyclic antidepressant medications such as amitriptyline and nortriptyline; selective serotonin and norepinephrine reuptake inhibitors such as duloxetine; and mexiletine. The agents may also include, for example, dopamine uptake inhibitors, monoamine oxidase inhibitors, norepinephrine uptake inhibitors, dopamine agonists, acetocholinesterase inhibitors, catechol O-methyltransferase inhibitors, anticholinergic agents, antioxidants, as well as synaptic and axonal enhancing medications.

While several exemplary embodiments of the present invention are discussed below, those skilled in the art will readily appreciate that various modifications may be made to these embodiments, and the invention is not limited to the specific electrode placements and pulse train patterns described therein.

First Exemplary Embodiment

Figure 3A:
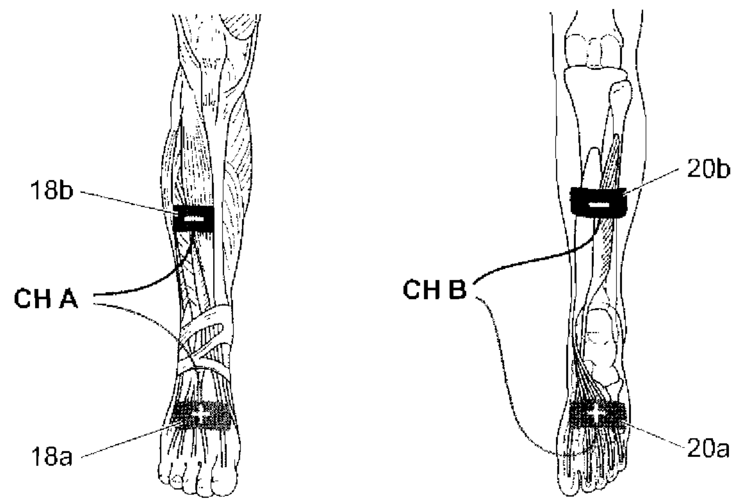
FIG. 3A illustrates a method for treating peripheral neuropathy in a patient by applying electrical stimulation in accordance with a first exemplary embodiment of the present invention.

In a first exemplary embodiment of the present invention, as generally illustrated in FIG. 3A, two pairs of electrodes are positioned in electrical contact with the patient's tissue in order to provide electrical stimulation to one or more of the muscles associated with toe and ankle dorsiflexion (or extension) and flexion (or plantar flexion) as a treatment for peripheral neuropathy in the lower extremities.

More specifically, as shown in FIG. 3A, a two-channel system is used to apply electrical stimulation to agonist/antagonist muscles involved in toe and ankle extension/flexion. For the first channel, a first electrode 18*a* is positioned in electrical contact with tissue to stimulate a motor point of the patient's extensor digitorum brevis muscle (extends the joints of the proximal phalanges of toes 1-4). Most preferably, first electrode 18*a* comprises a surface electrode that is positioned on the patient's skin on the dorsum of the foot over the first four metatarsal bones. A second electrode 18*b* is positioned in electrical contact with tissue to stimulate a motor point of the patient's tibialis anterior (extends foot at the ankle), extensor digitorum longus (extends toes 2-5 and the foot at the ankle), and/or extensor hallucis longus (extends toe 1 and the foot at the ankle) muscles. Most preferably, second electrode 18*b* comprises a surface electrode that is positioned on the patient's skin at the anterior lateral mid-shaft of the leg over the mid-tibialis anterior and the approximate mid-belly of the extensor digitorum longus and extensor hallucis longus muscles.

For the second channel, a first electrode 20*a* is positioned in electrical contact with tissue to stimulate motor points of the patient's intrinsic foot muscles. Most preferably, first electrode 20*a* comprises a surface electrode that is positioned on the patient's skin on the sole of the foot at the anterior one-third junction to include the abductor hallucis. A second electrode 20*b* is positioned in electrical contact with tissue to stimulate motor points of the patient's tibialis posterior (flexes the foot at the ankle) and flexor hallucis muscles. Most preferably, second electrode 20*b* comprises a surface electrode that is positioned on the patient's skin on the posterior distal one-third of the lower leg.

During treatment, the first and second channels are positioned on the right or left leg, and a patterned pulse train is applied to the leg as discussed more fully below. It will be appreciated that the muscles involved in toe and ankle extension/flexion may be bilaterally stimulated when the electrical stimulation device contains at least four channels. Alternatively, two electrical stimulation devices can be used for bilateral stimulation: one to stimulate the right leg, and one to stimulate the left leg.

In this exemplary embodiment, the pulse train pattern comprises a triphasic overlapping pulse train pattern having the following parameters:

Pulse duration of individual electrical pulses: 50-70 microseconds

Current amplitude of individual electrical pulses: 30-70 milliamps

Duration of first phase: 200 milliseconds

Duration of overlap between first and second phase: 40 milliseconds

Duration of second phase: 200 milliseconds

Duration of overlap between second and third phase: 40 milliseconds

Duration of third phase: 120 milliseconds

Frequency of pulse train pattern: 0.67 Hz

Total treatment time: 20 minutes

Total number of treatments: 18 during six weeks

Frequency of individual electrical pulses (in each phase): 50 Hz

Second Exemplary Embodiment

Figure 3B:
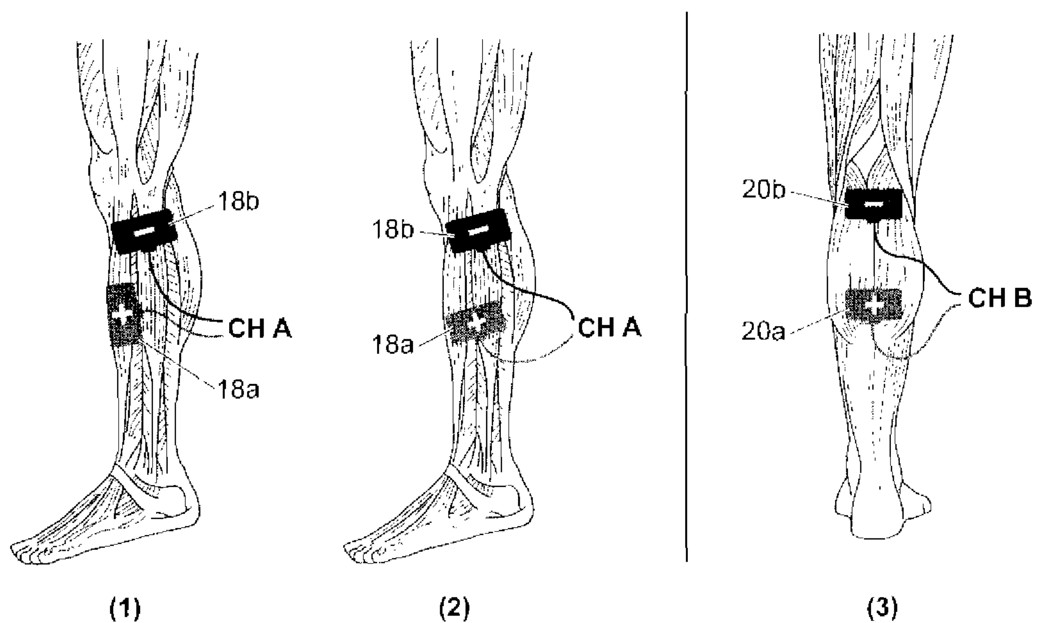
FIG. 3B illustrates a method for treating peripheral neuropathy in a patient by applying electrical stimulation in accordance with a second exemplary embodiment of the present invention.

In a second exemplary embodiment of the present invention, generally illustrated in FIG. 3B, two pairs of electrodes are positioned in electrical contact with the patient's tissue in order to provide electrical stimulation to one or more of the muscles associated with ankle dorsiflexion and plantar flexion and ankle eversion/inversion as a treatment for peripheral neuropathy in the lower extremities.

More specifically, as shown in FIG. 3B, a two-channel system is used to apply electrical stimulation to muscles involved in ankle dorsiflexion and plantar flexion and/or ankle inversion/eversion. For the first channel (panel 1 of FIG. 3B), a first electrode 18*a* is positioned in electrical contact with tissue to stimulate a motor point of the patient's lower portion of the tibialis anterior muscle. Most preferably, first electrode 18*a* comprises a surface electrode that is positioned on the patient's skin over the mid-belly of the tibialis anterior muscle. A second electrode 18*b* is positioned in electrical contact with tissue to stimulate a motor point of the patient's proximal tibialis anterior muscle. Most preferably, second electrode 18*b* comprises a surface electrode that is positioned on the patient's skin inferior to the fibular head.

Alternatively, for the first channel (panel 2 of FIG. 3B), a first electrode 18*a* is positioned in electrical contact with tissue to stimulate motor points of the patient's anterior and lateral muscles of the leg. Most preferably, first electrode 18*a* comprises a surface electrode that is positioned on the patient's skin at the mid-belly of the tibialis anterior as well as the peroneus muscles. A second electrode 18*b* is positioned in electrical contact with tissue to stimulate a motor point of the patient's proximal tibialis anterior muscle. Most preferably, second electrode 18*b* comprises a surface electrode that is positioned on the patient's skin inferior to the fibular head.

For the second channel (panel 3 of FIG. 3B), a first electrode 20*a* and a second electrode 20*b* are positioned in electrical contact with tissue to stimulate motor points of the patient's triceps surae (comprised of the gastrocnemius medial head (which plantar flexes the foot at the ankle), the gastrocnemius lateral head (which plantar flexes foot at the ankle), and/or the soleus muscle (which plantar flexes the foot at the ankle)). Most preferably, first electrode 20*a* comprises a surface electrode that is positioned on the patient's skin directly over the junction of the gastrocnemius and soleus muscles. Most preferably, second electrode 20*b* comprises a surface electrode that is positioned on the patient's skin posteriorly just inferior to the popliteal fossa over the tibial nerve and the two heads of the gastrocnemius muscle.

During treatment, the first and second channels are positioned on the right or left leg, and a patterned pulse train is applied to the leg as discussed more fully below. It will be appreciated that the muscles involved in ankle dorsiflexion and plantar flexion and/or ankle inversion/eversion may be bilaterally stimulated when the electrical stimulation device contains at least four channels. Alternatively, two electrical stimulation devices can be used for bilateral stimulation: one to stimulate the right leg, and one to stimulate the left leg.

In this exemplary embodiment, the pulse train pattern comprises a triphasic overlapping pulse train pattern having the following parameters:

Pulse duration of individual electrical pulses: 50-70 microseconds

Current amplitude of individual electrical pulses: 30-70 milliamps

Duration of first phase: 200 milliseconds

Duration of overlap between first and second phase: 40 milliseconds

Duration of second phase: 200 milliseconds

Duration of overlap between second and third phase: 40 milliseconds

Duration of third phase: 120 milliseconds

Frequency of pulse train pattern: 0.67 Hz

Total treatment time: 20 minutes

Total number of treatments: 18 during six weeks

Frequency of individual electrical pulses (in each phase): 50 Hz

Third Exemplary Embodiment

Figure 3C:
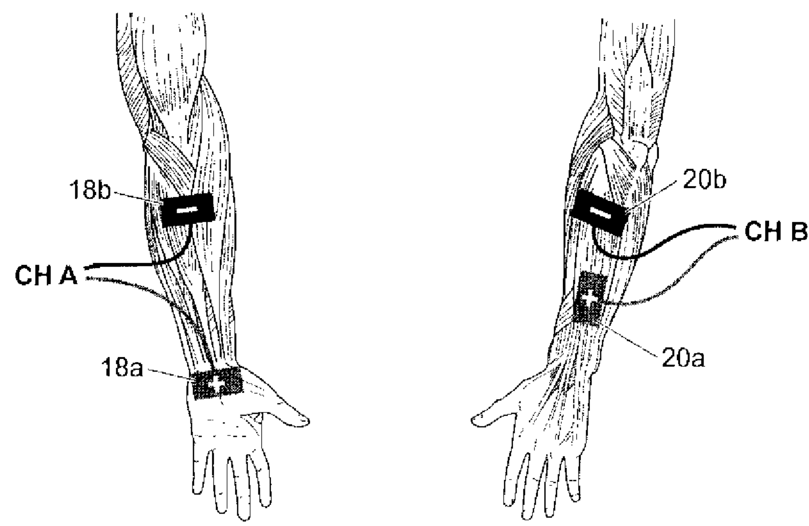
FIG. 3C illustrates a method for treating peripheral neuropathy in a patient by applying electrical stimulation in accordance with a third exemplary embodiment of the present invention.

In a third exemplary embodiment of the present invention, also generally illustrated in FIG. 3C, two pairs of electrodes are positioned in electrical contact with the patient's tissue in order to provide electrical stimulation to one or more of the muscles associated with wrist flexion/extension, wrist pronation/supination, and/or finger flexion/extension as a treatment for peripheral neuropathy in the upper extremities. The treated muscles include the flexor digitorum superficialis, flexor carpi radialis, flexor carpi ulnaris, extensor digitorum, extensor digiti minimi muscle, extensor carpi ulnaris, extensor carpi radialis longus, and/or extensor carpi radialis brevis.

More specifically, as shown in FIG. 3C, a two-channel system is used to apply electrical stimulation to muscles of the wrist and fingers. For the first channel, a first electrode 18*a* is positioned in electrical contact with tissue of the patient's proximal palmar surface to stimulate motor points of the patient's intrinsic hand muscles. Most preferably, first electrode 18*a* comprises a surface electrode that is positioned on the patient's skin across the thenar and the hypothenar eminence on the palmar/anterior side of the forearm arm at the base of the wrist just below the wrist crease. A second electrode 18*b* is positioned in electrical contact with tissue to stimulate motor points of the patient's volar-surface, proximal forearm muscles. Most preferably, second electrode 18*b* comprises a surface electrode that is positioned on the patient's skin on the palmar/anterior side of the lower arm just below the elbow joint.

For the second channel, a first electrode 20*a* is positioned in electrical contact with tissue to stimulate a motor point of the patient's extensor digitorum muscle (extends medial four digits at metacarpophalangeal joints, and extends the hand at the wrist) and pollicis muscles. Most preferably, first electrode 20*a* comprises a surface electrode that is positioned on the patient's skin on the dorsal/posterior side of the lower arm on the distal one-third between the wrist crease and the elbow joint. A second electrode 20*b* is positioned in electrical contact with a tissue to stimulate motor points of the patient's proximal extensor muscles of the forearm. Most preferably, second electrode **20*b*** comprises a surface electrode that is positioned on the patient's skin on the dorsal/posterior side of the lower arm just below the elbow joint.

During treatment, the first and second channels are positioned on the right or left arm, and a patterned pulse train is applied to the arm and wrist as discussed more fully below. It will be appreciated that the muscles involved in wrist and finger extension/flexion may be bilaterally stimulated when the electrical stimulation device contains at least four channels. Alternatively, two electrical stimulation devices can be used for bilateral stimulation: one to stimulate the right wrist and fingers, and one to stimulate the left wrist and fingers.

In this exemplary embodiment, the pulse train pattern comprises a triphasic overlapping pulse train pattern having the following parameters:

Pulse duration of individual electrical pulses: 50-70 microseconds

Current amplitude of individual electrical pulses: 30-70 milliamps

Duration of first phase: 100 milliseconds

Duration of overlap between first and second phases: 20 milliseconds

Duration of second phase: 100 milliseconds

Duration of overlap between second and third phases: 20 milliseconds

Duration of third phase: 60 milliseconds

Frequency of pulse train pattern: 0.67 Hz

Total treatment time: 20 minutes

Total number of treatments: 18 during six weeks

Frequency of individual electrical pulses (in each phase): 50 Hz

Fourth Exemplary Embodiment

Figure 3D:
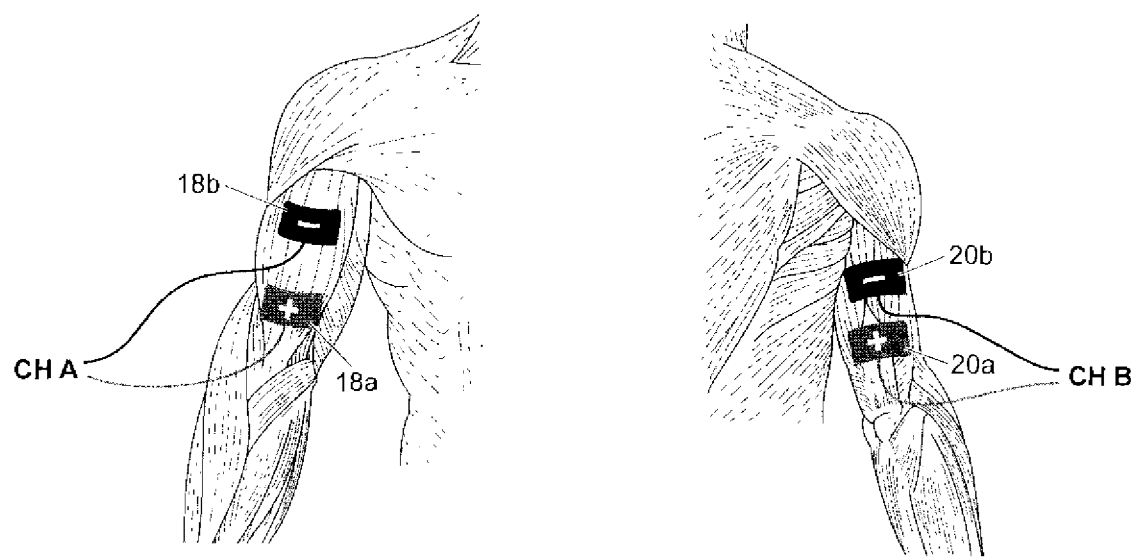
FIG. 3D illustrates a method for treating peripheral neuropathy in a patient by applying electrical stimulation in accordance with a fourth exemplary embodiment of the present invention.

In a fourth exemplary embodiment of the present invention, also generally illustrated in FIG. 3D, two pairs of electrodes are positioned in electrical contact with the patient's tissue in order to provide electrical stimulation to one or more of the muscles associated with elbow flexion/extension as a treatment for peripheral neuropathy in the upper extremities.

More specifically, as shown in FIG. 3D, a two-channel system is used to apply electrical stimulation to muscles of the upper arm. For the first channel, a first electrode **18*a* and a second electrode 18*b* are positioned in electrical contact with tissue to stimulate motor points of the patient's biceps brachii muscles (flex the forearm at the elbow). Most preferably, first electrode 18*a* comprises a surface electrode that is positioned on the patient's skin on the anterior side of the upper arm just above the insertion of the biceps brachii muscles. Most preferably, second electrode 18*b*** comprises a surface electrode that is positioned on the patient's skin on the anterior side of the upper arm just below the origin of the biceps brachii muscles.

For the second channel, a first electrode **20*a* and a second electrode 20*b* are positioned in electrical contact with tissue to stimulate motor points of the patient's triceps brachii muscles (extend the forearm at the elbow). Most preferably, first electrode 20*a* comprises a surface electrode that is positioned on the patient's skin on the posterior side of the upper arm above the insertion of the triceps brachii muscles. Most preferably, second electrode 20*b*** comprises a surface electrode that is positioned on the patient's skin on the posterior side of the upper arm below the origin of the triceps brachii muscles.

During treatment, the first and second channels are positioned on the right or left arm, and a patterned pulse train is applied to the upper arm as discussed more fully below. It will be appreciated that the muscles involved in elbow flexion/extension may be bilaterally stimulated when the electrical stimulation device contains at least four channels. Alternatively, two electrical stimulation devices can be used for bilateral stimulation: one to stimulate the right upper arm, and one to stimulate the left upper arm.

In this exemplary embodiment, the pulse train pattern comprises a triphasic overlapping pulse train pattern having the following parameters:

Pulse duration of individual electrical pulses: 50-70 microseconds

Current amplitude of individual electrical pulses: 30-70 milliamps

Duration of first phase: 100 milliseconds

Duration of overlap between first and second phases: 20 milliseconds

Duration of second phase: 100 milliseconds

Duration of overlap between second and third phases: 20 milliseconds

Duration of third phase: 60 milliseconds

Frequency of pulse train pattern: 0.67 Hz

Total treatment time: 20 minutes

Total number of treatments: 18 during six weeks

Frequency of individual electrical pulses (in each phase): 50 Hz

Fifth Exemplary Embodiment

Figure 3E:
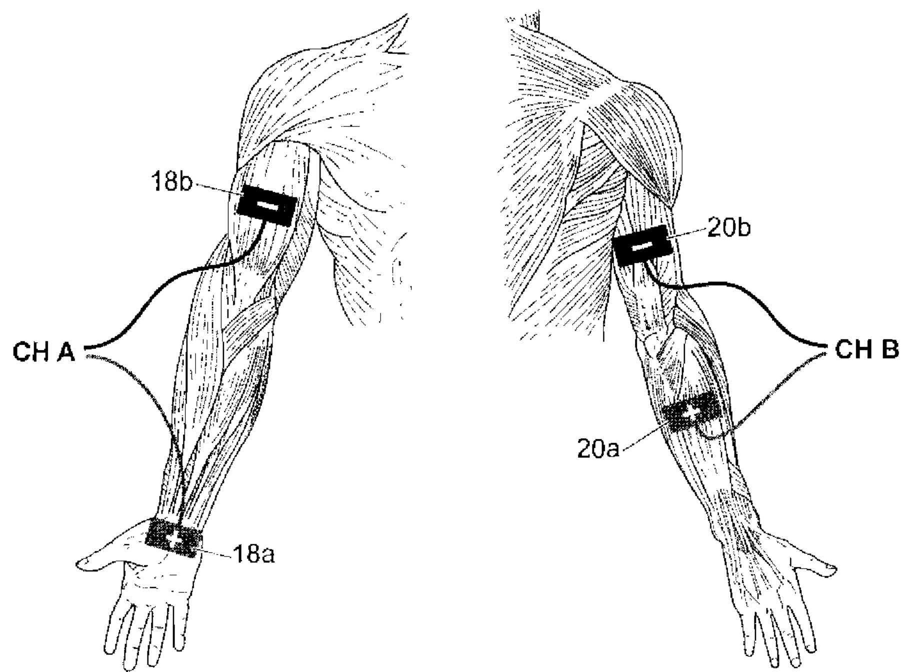
FIG. 3E illustrates a method for treating peripheral neuropathy in a patient by applying electrical stimulation in accordance with a fifth exemplary embodiment of the present invention.

In a fifth exemplary embodiment of the present invention, also generally illustrated in FIG. 3E, two pairs of electrodes are positioned in electrical contact with the patient's tissue in order to provide electrical stimulation to one or more of the muscles involved in movements of the upper extremities as a treatment for peripheral neuropathy in the upper extremities.

More specifically, as shown in FIG. 3E, a first pair of electrodes **18*a*, 18*b* provide stimulation to the anterior portion of the arm. A first electrode 18*a* is positioned in electrical contact with tissue of the proximal palmar surface to stimulate the patient's intrinsic hand muscles. Most preferably, first electrode 18*a* comprises a surface electrode that is positioned on the patient's skin across the thenar and hypothenar eminence of the palmar/anterior side of the forearm at the base of the wrist just below the wrist crease. A second electrode 18*b* is positioned in electrical contact with tissue to stimulate a motor point of the patient's biceps brachii muscles, the median nerve, and the ulnar nerve. Most preferably, second electrode 18*b*** comprises a surface electrode that is positioned on the patient's skin anterior and medially (to capture the median and ulnar nerve bundle) near the midpoint of the biceps brachii muscles.

Another pair of electrodes **20*a*, 20*b* is provided to stimulate the posterior muscles of the arm. A first electrode 20*a* is positioned in electrical contact with tissue to stimulate a motor point of the patient's proximal extensor muscles of the forearm. Most preferably, first electrode 20*a* comprises a surface electrode that is positioned on the patient's skin on the dorsal/posterior side of the lower arm just below the elbow joint. A second electrode 20*b* is positioned in electrical contact with tissue to stimulate a motor point of the patient's triceps brachii muscles. Most preferably, second electrode 20*b*** comprises a surface electrode that is positioned on the patient's skin on the posterior side of the arm near the midpoint of the triceps brachii muscles.

During treatment, the first and second channels are positioned on the right or left arm, and a patterned pulse train is applied to the arm and wrist as discussed more fully below. It will be appreciated that the muscles involved in arm movement may be bilaterally stimulated when the electrical stimulation device contains at least four channels. Alternatively, two electrical stimulation devices can be used for bilateral stimulation: one to stimulate the right arm, and one to stimulate the left arm.

In this exemplary embodiment, the pulse train pattern comprises a triphasic overlapping pulse train pattern having the following parameters:

Pulse duration of individual electrical pulses: 50-70 microseconds

Current amplitude of individual electrical pulses: 30-70 milliamps

Duration of first phase: 100 milliseconds

Duration of overlap between first and second phases: 20 milliseconds

Duration of second phase: 100 milliseconds

Duration of overlap between second and third phases: 20 milliseconds

Duration of third phase: 60 milliseconds

Frequency of pulse train pattern: 0.67 Hz

Total treatment time: 20 minutes

Total number of treatments: 18 during six weeks

Frequency of individual electrical pulses (in each phase): 50 Hz

Sixth Exemplary Embodiment

Figure 3F:
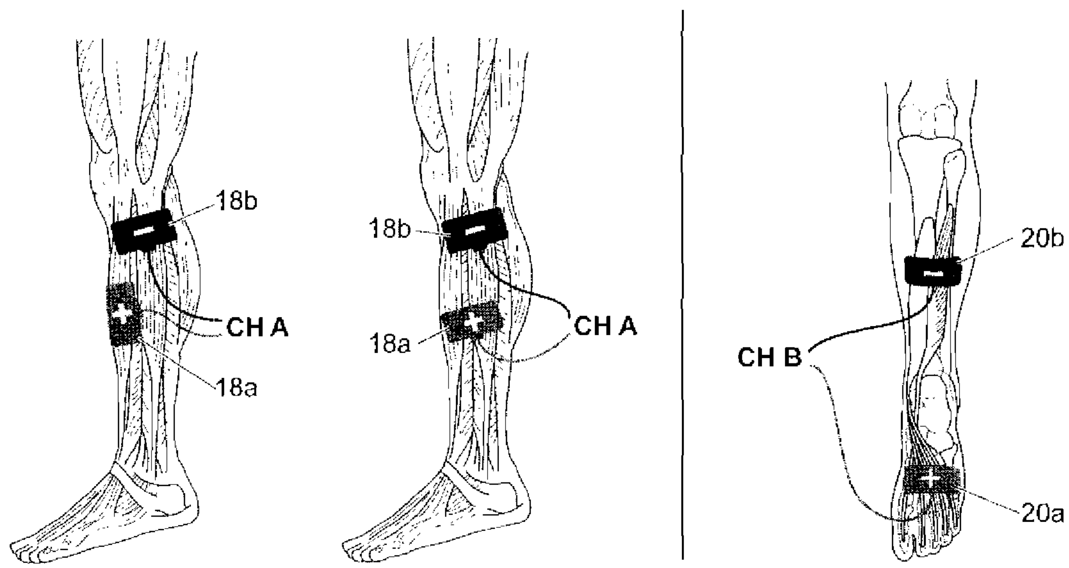
FIG. 3F illustrates a method for treating peripheral neuropathy in a patient by applying electrical stimulation in accordance with a sixth exemplary embodiment of the present invention.

In a sixth exemplary embodiment of the present invention, generally illustrated in FIG. 3F, two pairs of electrodes are positioned in electrical contact with the patient's tissue in order to provide electrical stimulation to one or more of the muscles associated with ankle and toe flexion/extension as a treatment for peripheral neuropathy in the lower extremities.

More specifically, as generally shown in FIG. 3F, a two-channel system is used to apply electrical stimulation to muscles involved in ankle and toe flexion/extension. For the first channel (panel 1 of FIG. 3F), a first electrode 18*a* is positioned in electrical contact with tissue to stimulate a motor point of the patient's lower portion of the tibialis anterior muscle. Most preferably, first electrode 18*a* comprises a surface electrode that is positioned on the patient's skin over the mid-belly of the tibialis anterior muscle. A second electrode 18*b* is positioned in electrical contact with tissue to stimulate a motor point of the patient's proximal tibialis anterior muscle. Most preferably, second electrode 18*b* comprises a surface electrode that is positioned on the patient's skin inferior to the fibular head.

Alternatively, for the first channel (panel 2 of FIG. 3F), a first electrode 18*a* is positioned in electrical contact with tissue to stimulate motor points of the patient's anterior and lateral muscles of the leg. Most preferably, first electrode 18*a* comprises a surface electrode that is positioned on the patient's skin at the mid-belly of the tibialis anterior as well as the peroneus muscles. A second electrode 18*b* is positioned in electrical contact with tissue to stimulate a motor point of the patient's proximal tibialis anterior muscle. Most preferably, second electrode 18*b* comprises a surface electrode that is positioned on the patient's skin inferior to the fibular head.

For the second channel (panel 3 of FIG. 3F), a first electrode 20*a* is positioned in electrical contact with tissue to stimulate motor points of the patient's intrinsic foot muscles. Most preferably, first electrode 20*a* comprises a surface electrode that is positioned on the patient's skin on the sole of the foot at the anterior one-third junction to include the abductor hallucis. A second electrode 20*b* is positioned in electrical contact with tissue to stimulate motor points of the patient's tibialis posterior (flexes the foot at the ankle) and flexor hallucis muscles. Most preferably, second electrode 20*b* comprises a surface electrode that is positioned on the patient's skin on the posterior distal one-third of the lower leg.

During treatment, the first and second channels are positioned on the right or left leg, and a patterned pulse train is applied to the leg as discussed more fully below. It will be appreciated that the muscles involved in ankle and toe flexion/extension may be bilaterally stimulated when the electrical stimulation device contains at least four channels. Alternatively, two electrical stimulation devices can be used for bilateral stimulation: one to stimulate the right leg, and one to stimulate the left leg.

In this exemplary embodiment, the pulse train pattern comprises a triphasic overlapping pulse train pattern having the following parameters:

Pulse duration of individual electrical pulses: 50-70 microseconds

Current amplitude of individual electrical pulses: 30-70 milliamps

Duration of first phase: 200 milliseconds

Duration of overlap between first and second phase: 40 milliseconds

Duration of second phase: 200 milliseconds

Duration of overlap between second and third phase: 40 milliseconds

Duration of third phase: 120 milliseconds

Frequency of pulse train pattern: 0.67 Hz

Total treatment time: 20 minutes

Total number of treatments: 18 during six weeks

Frequency of individual electrical pulses (in each phase): 50 Hz

Seventh Exemplary Embodiment

Figure 3G:
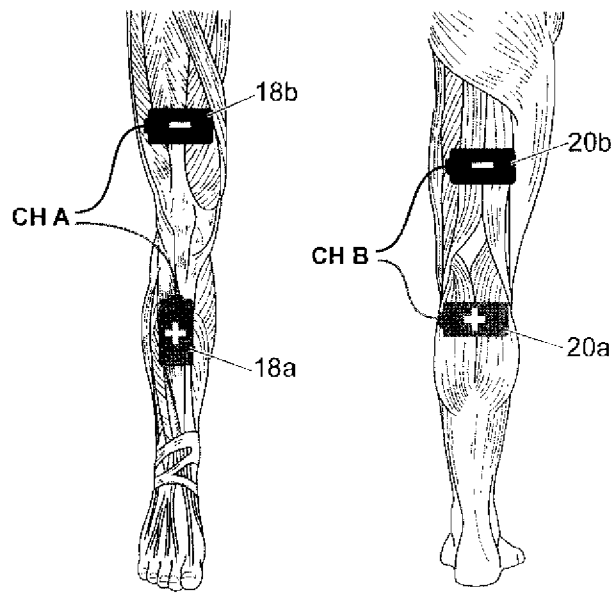
FIG. 3G illustrates a method for treating peripheral neuropathy in a patient by applying electrical stimulation in accordance with a seventh exemplary embodiment of the present invention.

In a seventh exemplary embodiment of the present invention, also generally illustrated in FIG. 3G, two pairs of electrodes are positioned in electrical contact with the patient's tissue in order to provide electrical stimulation to one or more of the muscles associated with the lower extremities as a treatment for peripheral neuropathy in the lower extremities.

More specifically, as generally shown in FIG. 3G, a two-channel system is used to apply electrical stimulation to muscles involved in leg movement. For the first channel, a first electrode 18*a* is positioned in electrical contact with tissue to stimulate a motor point of the patient's proximal tibialis anterior muscle. Most preferably, first electrode 18*a* comprises a surface electrode that is positioned on the patient's skin on the anterior side of the leg and inferior to the fibular head. A second electrode 18*b* is positioned in electrical contact with tissue to stimulate a motor point near the midpoint of a patient's quadriceps muscles. Most preferably, second electrode 18*b* comprises a surface electrode that is positioned on the patient's skin on the anterior side of the leg just above the knee.

For the second channel, a first electrode 20*a* is positioned in electrical contact with tissue to stimulate a motor point of the patient's triceps surae muscles. Most preferably, first electrode 20*a* comprises a surface electrode that is positioned on the patient's skin on the posterior side of the lower leg near the midpoint of the gastrocnemius muscle. The second electrode 20*b* is positioned in electrical contact with a tissue to stimulate a motor point of the patient's mid-hamstrings. Most preferably, second electrode 20*b* comprises a surface electrode that is positioned on the patient's skin on the distal one third of the posterior side of the leg.

During treatment, the first and second channels are positioned on the right or left leg, and a patterned pulse train is applied to the leg as discussed more fully below. It will be appreciated that the muscles involved in leg movement may be bilaterally stimulated when the electrical stimulation device contains at least four channels. Alternatively two electrical stimulation devices can be used for bilateral stimulation: one to stimulate the right leg, and one to stimulate the left leg.

In this exemplary embodiment, the pulse train pattern comprises a triphasic overlapping pulse train pattern having the following parameters:

Pulse duration of individual electrical pulses: 50-100 microseconds

Current amplitude of individual electrical pulses: 30-90 milliamps

Duration of first phase: 200 milliseconds

Duration of overlap between first and second phases: 40 milliseconds

Duration of second phase: 200 milliseconds

Duration of overlap between second and third phases: 40 milliseconds

Duration of third phase: 120 milliseconds

Frequency of pulse train pattern: 0.67 Hz

Total treatment time: 20 minutes

Total number of treatments: 18 during six weeks

Frequency of individual electrical pulses (in each phase): 50 Hz

Eighth Exemplary Embodiment

Figure 3H:
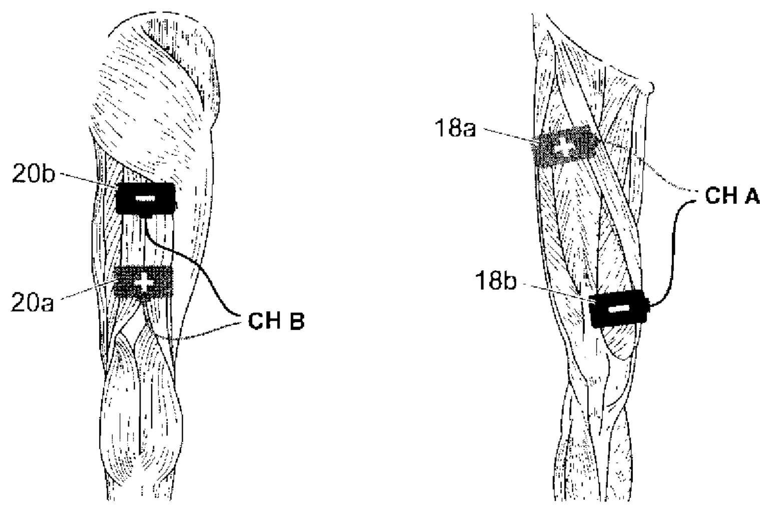
FIG. 3H illustrates a method for treating peripheral neuropathy in a patient by applying electrical stimulation in accordance with an eighth exemplary embodiment of the present invention.

In an eighth exemplary embodiment of the present invention, also generally illustrated in FIG. 3H, two pairs of electrodes are positioned in electrical contact with the patient's tissue in order to provide electrical stimulation to one or more of the muscles associated with knee extension/flexion as a treatment for peripheral neuropathy in the lower extremities.

More specifically, as generally shown in FIG. 3H, a two-channel system is used to apply electrical stimulation to muscles involved in knee extension/flexion. For the first channel, a first electrode 18*a* is positioned in electrical contact with tissue to stimulate a motor point of the patient's rectus femoris (extends leg at the knee) and vastus lateralis (extends leg at the knee) muscles. Most preferably, first electrode 18*a* comprises a surface electrode that is positioned on the patient's skin on the proximal one third of the anterior side of the upper leg. A second electrode 18*b* is positioned in electrical contact with tissue to stimulate the motor point of the patient's vastus medialis muscle (extends the leg at the knee). Most preferably, second electrode 18*b* comprises a surface electrode that is positioned on the patient's skin on the anterior medial side of the upper leg just above the knee.

For the second channel, a first electrode 20*a* is positioned in electrical contact with tissue to stimulate a motor point of the patient's distal portion of the biceps femoris muscle (flexes the leg at the knee), semimembranosus muscle (flexes the leg at the knee), and/or semitendinosus muscle (flexes the leg at the knee). Most preferably, first electrode 20*a* comprises a surface electrode that is positioned on the patient's skin on the posterior side of the upper leg just above the knee. A second electrode 20*b* is positioned in electrical contact with a tissue to stimulate a motor point of the patient's proximal portion of the biceps femoris, semimembranosus, and/or semitendinosus muscles. Most preferably, second electrode 20*b* comprises a surface electrode that is positioned on the patient's skin on the proximal one third of the posterior side of the upper leg.

During treatment, the first and second channels are positioned on the right or left leg, and a patterned pulse train is applied to the leg as discussed more fully below. It will be appreciated that the muscles involved in knee flexion/extension may be bilaterally stimulated when the electrical stimulation device contains at least four channels. Alternatively, two electrical stimulation devices can be used for bilateral stimulation: one to stimulate the right leg, and one to stimulate the left leg.

In this exemplary embodiment, the pulse train pattern comprises a triphasic overlapping pulse train pattern having the following parameters:

Pulse duration of individual electrical pulses: 50-200 microseconds

Current amplitude of individual electrical pulses: 30-140 milliamps

Duration of first phase: 200 milliseconds

Duration of overlap between first and second phases: 40 milliseconds

Duration of second phase: 200 milliseconds

Duration of overlap between second and third phases: 40 milliseconds

Duration of third phase: 120 milliseconds

Frequency of pulse train pattern: 0.67 Hz

Total treatment time: 20 minutes

Total number of treatments: 18 during six weeks

Frequency of individual electrical pulses (in each phase): 50 Hz

Peripheral Neuropathy Case Study 1

The first case study involved a 79 year-old male with two year history of progressive numbness and decreased lower extremity coordination diagnosed as large fiber sensory motor neuropathy not related to diabetes. The initial evaluation demonstrated an otherwise well nourished and well spoken male who walked with a cane for functional distances because of poor balance and coordination. Pain and significant weakness were not associated symptoms. The patient's ankle strength was 4/5 in eversion and dorsiflexion, and knee strength was 5/5 using a standard manual muscle test. The patient's standing balance with eyes closed was very difficult with significant sway. Nerve conduction velocity of the peroneal nerves and tibial nerves showed distal conduction slowing of the motor segments without proximal slowing. The conduction was measured with a Nerve Conduction Velocity Test using an EMG testing system.

A two-channel EMG patterned electrical stimulation application to the leg and foot as generally shown in FIG. 3A and described in the first embodiment of the present invention. The protocol involved placement of the first channel with the negative electrode on the nerve and muscles of the anterior tibialis and peroneal brevis and longus of the anterior-lateral aspect of the leg. The relatively positive electrode placed across the dorsum of the foot to activate the deep and superficial branches of the sensory portion of the peroneal nerve.

The second channel negative electrode was placed across the proximal portion of the gastrocnemius muscle to incorporate the tibial nerve. The relatively positive electrode was placed transverse over the medial aspect of the plantar surface of the foot to incorporate the medial and lateral branches of the tibial nerve and the abductor hallucis and other foot intrinsic muscles.

The intensity of the stimulation was increased until the patient could sense activation of the proximal aspect of the leg, both anterior and posterior. The intensity was approximately 60 mA. No stimulation was felt in the region of the foot. After five minutes of this sensory level of stimulation, the intensity was increased to the point that the abductor hallucis muscle produced a twitch and the gastrocnemius muscle also demonstrated a consistent twitch. The intensity was approximately 70 mA. The electrical stimulation patterns were as follows:

Pulse duration of individual electrical pulses: 70 microseconds

Current amplitude of individual electrical pulses: 60-70 milliamps

Duration of first phase: 200 milliseconds

Duration of overlap between first and second phases: 40 milliseconds

Duration of second phase: 200 milliseconds

Duration of overlap between second and third phases: 40 milliseconds

Duration of third phase: 120 milliseconds

Frequency of pulse train pattern: 0.67 Hz

Total treatment time: 20 minutes

Total number of treatments: 9 during three weeks

Frequency of individual electrical pulses (in each phase): 50 Hz

The stimulation on the anterior lateral aspect of the leg was able to activate the peroneal muscles but not the anterior tibialis muscle. The dorsal intrinsic muscle of the foot did not exist in this patient and thus, was not activated.

The treatments were well tolerated with no increase in symptoms. After the second session, the patient noted a significant change in the anatomical level of touch and pin sensation of the leg (using the Semmes Weinstein Test) with the most proximal site of first sensation moving from approximately 2 cm below the knee joint (both anterior and posterior) down to just above the ankle malleoli of approximately 1 cm. On re-testing, the level remained stable. With a total of six repeated treatments, the level of touch and pin sensation did not pass the level of the ankle. Ambulation improved to the point where the cane was no longer required for functional distances.

The pain sensation at rest and with walking reduced from a score of 6.4 on the visual analogue scale to a level of 1.2. This level of improved comfort lasted for six weeks after the electrical stimulation protocol ceased. The pain gradually increased back to baseline after another three months. Likewise, ambulation slowed for improved balance, but then the patient resumed using a cane as an assistive device.

Peripheral Neuropathy Case Study 2

This case study involved a 54 year-old male with diabetic peripheral neuropathy and burning pain. The patient's serum glucose levels were noted to be under good control with diet and oral hypoglycemic medications. The patient's hemoglobin A1c was 5.7. The patient exhibited bilateral foot and ankle pain, which interfered with walking and sleep. The pain was noted to be at a Visual Analogue scale level of 8.2 before treatment. The patient indicated that sensation at the bottom of both feet felt partially numb using the Semmes Weinstein test using a 4.56 gram monofilament indicating diminished protective sensation. The electrodes were placed in the same position as Case Study No. 1. The electrical stimulation patterns were as follows:

Pulse duration of individual electrical pulses: 70 microseconds

Current amplitude of individual electrical pulses: 55 milliamps

Duration of first phase: 200 milliseconds

Duration of overlap between first and second phases: 40 milliseconds

Duration of second phase: 200 milliseconds

Duration of overlap between second and third phases: 40 milliseconds

Duration of third phase: 120 milliseconds

Frequency of pulse train pattern: 0.67 Hz

Total treatment time: 20 minutes

Total number of treatments: 12 during six weeks

Following the end of the first 20 minutes treatment, the pain level was reduced to 4.3. After the first 30 minutes of treatment, the pain level was further reduced to a 3.6 and remained at that level for six hours. After the third treatment, pain levels were reduced to 1.8 and remained at or close to that level for the next six hours. The patient also reported improved sleep.

After six treatments at two sessions per week, the pain continued to be noted to fluctuate between 1.5 and 3.5 throughout the day and night. The sensation of numbness at the bottom of the feet was reversed (evidenced by Semmes Weinstein Test in which the 3.61 g indicated normal sensation).

After this, the treatments were reduced to one 20-minute treatment each week to 10 days. The pain reduction and sensation improvement was maintained for two months with intermittent treatment. During this time, the patient's diabetes remained under control.

Peripheral Neuropathy Case Study 3

This case study involved a 50 year-old male with 12 years of peripheral neuropathy due to vasculopathy worse following tarsal tunnel release. The man was unable to sleep more than two hours. The patient had an abnormally slow gait, and he required a cane for distances. The patient's gait speed was 19 seconds (normal is 9 seconds over this distance of 30 feet×2 with a turn-around).

Nerve conduction velocity testing showed some slowing plus conduction block at low intensities across both ankles—partial loss of conduction and decreased compound muscle action potential (CMAP) indicating reduced sensation and motor control.

The patient was taking narcotic analgesics (Vicodin 7.5 mg four times daily and 15 mg at night) and anti-coagulation drug (Coumadin INR 2.5 consistent). Tizanadine (alpha norepinephrine agonist) was added at 6 mg QHS. The patient exhibited an initial pain reduction of 8.2 to 7.3 on Tizanadine alone for one week.

A two-channel EMG patterned electrical stimulation application to the leg and foot as generally shown in FIG. 3A and described in the first embodiment of the present invention. The first channel relative negative electrode was applied to the anterior tibialis and peroneals muscles and nerves, and the relative positive electrode was applied to the dorsum of foot. The second channel relative negative electrode was applied to the gastrocnemius muscle and tibial nerve with the relatively positive electrode to the abductor hallucis of the medial aspect of the arch of the foot. The electrical stimulation patterns were as follows:

Pulse duration of individual electrical pulses: 70 microseconds

Current amplitude of individual electrical pulses: 45-50 milliamps

Duration of first phase: 200 milliseconds

Duration of overlap between first and second phases: 40 milliseconds

Duration of second phase: 200 milliseconds

Duration of overlap between second and third phases: 40 milliseconds

Duration of third phase: 120 milliseconds

Frequency of pulse train pattern: 0.67 Hz

Total treatment time: 20 minutes

Total number of treatments: 6 during three weeks

Frequency of individual electrical pulses (in each phase): 50 Hz

Sensory stimulation was applied to the patient only five minutes as in Case Study No. 1. Following that, intensity was increased to obtain minimal motor twitch activation of the gastrocnemius and abductor hallucis muscles for an additional 15 minutes two times per week.

After treatment, the gait speed improved from 19 seconds to 11 (9 seconds normal for height and age). The patient exhibited no antalgia during gait, and was able to walk without the use of cane or assistive device. Further, the patient was able to work through day with only occasional rest periods. In addition, the patient had reduced pain of 7.3 to 2.4 after six sessions. The patient had touch sensation at the bottoms of his feet improved significantly without hyperalgesia. At a six-month follow-up, the patient required only occasional treatments as above to maintain an adequate reduction of pain. Analgesic medication were also cut in half and the Tizanadine was discontinued.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

Then invention claimed is:

1. A method for treating reduced sensation associated with peripheral neuropathy caused by diabetes in a diabetic patient comprising:

applying neuromuscular electrical stimulation having a triphasic pulse train pattern to a peripheral target body region selected from said patient's, arm, forearm, wrist, hand, thigh, lower leg, ankle, and foot, wherein said step of applying neuromuscular electrical stimulation having a triphasic pulse train pattern comprises:

providing a first channel comprising two electrodes, wherein a first electrode of said first channel is positioned in electrical contact with tissue of a first target body region of said patient and a second electrode of said first channel is positioned in electrical contact with tissue of a second target body region of said patient;

providing a second channel comprising two electrodes, wherein a first electrode of said second channel is positioned in electrical contact with tissue of a third target body region of said patient and a second electrode of said second channel is positioned in electrical contact with tissue of a fourth target body region of said patient; and applying a series of electrical pulses having said triphasic pulse train pattern to said first, second, third, and fourth target body regions of said patient through said first and second channels in accordance with a procedure for treating peripheral neuropathy, wherein said series of electrical pulses comprises a plurality of cycles of a triphasic sequential pulse train pattern, wherein said triphasic sequential pulse train pattern comprises a first phase of electrical pulses applied to said first channel, a second phase of electrical pulses applied to said second channel, and a third phase of electrical pulses applied to said first channel, and wherein said second phase of electrical pulses commences after termination of said first phase of electrical pulses and said third phase of electrical pulses commences after termination of said second phase of electrical pulses; and wherein said step of applying neuromuscular electrical stimulation improves sensation in said patient and wherein said improved sensation in said patient is determined using a monofilament test or an improved vibration perception test measured using a tool selected from the group consisting of a tuning fork and a biothesiometer.

2. The method of claim 1, wherein said first electrode of said first channel is positioned so as to stimulate an extensor digitorum brevis muscle of said patient, and said second electrode of said first channel is positioned so as to stimulate an anterior tibialis muscle, an extensor digitorum longus muscle, and/or an extensor hallucis longus muscle of said patient; and wherein said first electrode of said second channel is positioned so as to stimulate an intrinsic foot muscle of said patient, and said second electrode of said second channel is positioned so as to stimulate a posterior tibialis muscle and a flexor hallucis muscle of said patient.

3. The method of claim 1, wherein said first and second electrodes of said first channel are positioned so as to stimulate a tibialis anterior muscle and an optional peroneus muscle of said patient; and wherein said first and second electrodes of said second channel are positioned so as to stimulate a triceps surae of said patient.

4. The method of claim 1, wherein said first electrode of said first channel is positioned so as to stimulate a flexor muscle of a hand of said patient selected from the group consisting of flexor digitorum superficialis and flexor digitorum profundus, and said second electrode of said first channel is positioned so as to stimulate a flexor muscle of a wrist of said patient selected from the group consisting of flexor carpi ulnaris and flexor carpi radialis; and wherein said first electrode of said second channel is positioned so as to stimulate an extensor muscle of said hand of said patient selected from the group consisting of extensor digitorum and extensor digiti minimi, and said second electrode of said second channel is of an arm of said patient; and wherein said first and second electrodes of said second channel are positioned so as to positioned so as to stimulate an extensor muscle of said wrist of said patient selected from the group consisting of extensor carpi ulnaris and extensor carpi radialis.

5. The method of claim 1, wherein said first and second electrodes of said first channel are positioned so as to a stimulate biceps brachii muscle stimulate a triceps brachii muscle of said arm of said patient.

6. The method of claim 1, wherein said first electrode of said first channel is positioned so as to stimulate a flexor muscle of a hand of said patient, and said second electrode of said first channel is positioned so as to stimulate a biceps brachii muscle of an arm of said patient; and wherein said first electrode of said second channel is positioned so as to stimulate an extensor forearm muscle of said arm of said patient, and said second electrode of said second channel is positioned so as to stimulate a triceps brachii muscle of said arm of said patient.

7. The method of claim 1, wherein said first and second electrodes of said first channel are positioned so as to stimulate a tibialis anterior muscle and an optional peroneus muscle of said patient; and wherein said first electrode of said second channel is positioned so as to stimulate the patient's intrinsic foot muscles on the sole of the foot, and said second electrode of said second channel is positioned so as to stimulate motor points of the patient's tibialis posterior and flexor hallucis muscles of said patient.

8. The method of claim 1, wherein said first electrode of said first channel is positioned so as to stimulate a tibialis anterior muscle of said patient, and said second electrode of said first channel is positioned so as to stimulate a quadriceps muscle of a leg of said patient; and wherein said first electrode of said second channel is positioned so as to stimulate a triceps surae of said patient, and said second electrode of said second channel is positioned so as to stimulate a hamstring muscle of said leg of said patient.

9. The method of claim 1, wherein said first electrode of said first channel is positioned so as to stimulate a rectus femoris muscle and/or a vastus lateralis muscle of a leg of said patient, and said second electrode of said first channel is positioned so as to stimulate a vastus medialis muscle of said leg of said patient; and wherein said first and second electrodes of said second channel are positioned so as to stimulate a biceps femoris muscle, a semimembranosus muscle, and/or a semitendinosus muscle of said leg of said patient.

10. The method of claim 1, wherein said improved sensation in said patient is determined using a monofilament test.

11. The method of claim 1, wherein said improved sensation in said patient is determined by improved vibration perception measured using a tool selected from the group consisting of a tuning fork and a biothesiometer.

12. The method of claim 1, further comprising the step of co-administering to said patient a therapeutically effective amount of an agent selected from the group consisting of corticosteroids, IV immunoglobulins, immunosuppressive agents, aldose reductase inhibitors, fish oil, gamma-linolenic acid, gangliosides, lipoic acid, myoinositol, nerve growth factor, protein kinase C inhibitors, pyridoxine, ruboxistaurin mesylate, thiamine, vitamin B12, codeine, gabapentin, topiramate, pregabalin, carbamazepine, phenytoin, lidocaine, amitriptyline, nortriptyline, duloxetine, and mexiletine.

13. The method of claim 1, further comprising the step of co-administering to said patient a therapeutically effective amount of an agent selected from the group consisting of dopamine uptake inhibitors, monoamine oxidase inhibitors, norepinephrine uptake inhibitors, dopamine agonists, acetocholinesterase inhibitors, catechol O-methyltransferase inhibitors, anticholinergic agents, antioxidants, and synaptic and axonal enhancing medications.

14. The method of claim 1, wherein said triphasic pulse train pattern comprises a series of electrical pulses each having a pulse duration of between 30 microseconds and 100 microseconds.

15. The method of claim 1, wherein said triphasic pulse train pattern comprises a series of electrical pulses each having a current amplitude of between 25 milliamps and 140 milliamps.

16. The method of claim 1, wherein said triphasic pulse train pattern comprises a series of electrical pulses each having a frequency of between 30 Hz and 100 Hz.

17. The method of claim 1, wherein each of said electrical pulse train patterns has a duration of between 100 microseconds and 200 microseconds.

18. The method of claim 1 wherein said step of applying neuromuscular electrical stimulation triggers p-type calcium channels.

19. A method for treating reduced sensation associated with peripheral neuropathy caused by diabetes in a diabetic patient comprising:

applying neuromuscular electrical stimulation having a biphasic or triphasic pulse train pattern to a peripheral target body region selected from said patient's, arm, forearm, wrist, hand, thigh, lower leg, ankle, and foot, said biphasic or triphasic pulse train pattern having a series of electrical pulses with a pulse duration between 30 and 200 microseconds, a current amplitude of 25 to 140 milliamps, and a frequency of 30 Hz to 100 Hz; and wherein said step of applying neuromuscular electrical stimulation improves sensation in said patient and wherein said improved sensation in said patient is determined using a monofilament test or an improved vibration perception test measured using a tool selected from the group consisting of a tuning fork and a biothesiometer.

20. The method of claim 19 wherein said pulse train pattern is biphasic.

21. The method of claim 19 wherein said pulse train pattern is triphasic.

22. The method of claim 19, wherein said series of electrical pulses comprises a plurality of cycles of a biphasic sequential pulse train pattern; and wherein said biphasic sequential pulse train pattern comprises a first phase of electrical pulses applied to said first channel and a second phase of electrical pulses applied to said second channel, and wherein said second phase of electrical pulses commences after termination of said first phase of electrical pulses.

23. The method of claim 19, wherein said series of electrical pulses comprises a plurality of cycles of a biphasic overlapping pulse train pattern; and wherein said biphasic overlapping pulse train pattern comprises a first phase of electrical pulses applied to said first channel and a second phase of electrical pulses applied to said second channel, and wherein said second phase of electrical pulses commences before termination of said first phase of electrical pulses.

24. The method of claim 19, wherein said series of electrical pulses comprises a plurality of cycles of a triphasic overlapping pulse train pattern;

wherein said triphasic overlapping pulse train pattern comprises a first phase of electrical pulses applied to said first channel, a second phase of electrical pulses applied to said second channel, and a third phase of electrical pulses applied to said first channel; and wherein said second phase of electrical pulses commences before termination of said first phase of electrical pulses and said third phase of electrical pulses commences before termination of said second phase of electrical pulses.

25. A method for treating reduced sensation associated with peripheral neuropathy caused by diabetes in a diabetic patient comprising:

applying neuromuscular electrical stimulation having a biphasic or triphasic pulse train pattern to a peripheral target body region selected from said patient's, arm, forearm, wrist, hand, thigh, lower leg, ankle, and foot, wherein said biphasic or triphasic pulse train pattern comprises a series of electrical pulses each having a current amplitude of between 25 milliamps and 140 milliamps; and wherein said step of applying neuromuscular electrical stimulation improves sensation in said patient and wherein said improved sensation in said patient is determined using a monofilament test or an improved vibration perception test measured using a tool selected from the group consisting of a tuning fork and a biothesiometer.

26. A method for treating reduced sensation associated with peripheral neuropathy caused by diabetes in a diabetic patient comprising:

applying neuromuscular electrical stimulation having a biphasic or triphasic pulse train pattern to a peripheral target body region selected from said patient's, arm, forearm, wrist, hand, thigh, lower leg, ankle, and foot, wherein each of said electrical pulse train patterns has a duration of between 100 microseconds and 200 microseconds; and wherein said step of applying neuromuscular electrical stimulation improves sensation in said patient and wherein said improved sensation in said patient is determined using a monofilament test or an improved vibration perception test measured using a tool selected from the group consisting of a tuning fork and a biothesiometer.

* * * * *